United States Patent
Lucet-Levannier et al.

(10) Patent No.: US 11,433,008 B2
(45) Date of Patent: Sep. 6, 2022

(54) COMPOSITION COMPRISING PHOTONIC PARTICLES, AT LEAST ONE ABSORBER AND AT LEAST ONE SURFACTANT

(71) Applicant: L'OREAL, Paris (FR)

(72) Inventors: Karine Lucet-Levannier, Rueil-Malmaison (FR); Jean-Dominique Bazin De Bezons, Montrouge (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/066,859

(22) PCT Filed: Dec. 28, 2016

(86) PCT No.: PCT/EP2016/082785
§ 371 (c)(1),
(2) Date: Jun. 28, 2018

(87) PCT Pub. No.: WO2017/114869
PCT Pub. Date: Jul. 6, 2017

(65) Prior Publication Data
US 2019/0008731 A1    Jan. 10, 2019

(30) Foreign Application Priority Data
Dec. 29, 2015 (FR) ...................... 1563419

(51) Int. Cl.
| | | |
|---|---|---|
| *A61K 8/02* | (2006.01) | |
| *A61K 8/25* | (2006.01) | |
| *A61Q 17/04* | (2006.01) | |
| *A61K 8/894* | (2006.01) | |
| *A61Q 19/02* | (2006.01) | |
| *A61Q 19/08* | (2006.01) | |
| *A61K 9/06* | (2006.01) | |
| *A61K 9/00* | (2006.01) | |
| *A61K 47/10* | (2017.01) | |

(52) U.S. Cl.
CPC ................ *A61K 8/025* (2013.01); *A61K 8/25* (2013.01); *A61K 8/894* (2013.01); *A61Q 17/04* (2013.01); *A61Q 19/02* (2013.01); *A61Q 19/08* (2013.01); *A61K 9/0014* (2013.01); *A61K 9/06* (2013.01); *A61K 47/10* (2013.01); *A61K 2800/31* (2013.01); *A61K 2800/412* (2013.01); *A61K 2800/413* (2013.01)

(58) Field of Classification Search
CPC .. A61K 8/025; A61K 2800/412; A61Q 19/02; A61Q 17/04
See application file for complete search history.

(56) References Cited

U.S. PATENT DOCUMENTS

| | | | | |
|---|---|---|---|---|
| 8,992,895 B2 * | 3/2015 | Halpern | ................. | A61Q 17/04 424/59 |
| 2012/0244202 A1* | 9/2012 | Simonnet | ............... | A61Q 17/04 977/773 |
| 2012/0282310 A1* | 11/2012 | Lucet-Levannier | ... | A61Q 17/04 424/59 |

FOREIGN PATENT DOCUMENTS

| | | |
|---|---|---|
| FR | 2 951 076 A1 | 4/2011 |
| FR | 2 951 077 A1 | 4/2011 |
| FR | 2 951 078 A1 | 4/2011 |
| FR | 2 956 315 A1 | 8/2011 |
| JP | 11-21223 A | 1/1999 |
| JP | 2013-507353 A | 3/2013 |
| JP | 2015-83561 A | 4/2015 |

OTHER PUBLICATIONS

ClearCo (http://www.clearcoproducts.com/dimethicones-peg12.html) available online Aug. 10, 2014, p. 1 (Year: 2014).*

(Continued)

*Primary Examiner* — Andrew S Rosenthal
(74) *Attorney, Agent, or Firm* — Oblon, McClelland, Maier & Neustadt, L.L.P.

(57) ABSTRACT

The present invention relates to a composition, especially a cosmetic composition, particularly a photoprotective composition, comprising at least: —photonic particles having an average size comprised from 0.5 μm to 100 μm and each including an arrangement that diffracts monodisperse nanoparticles or voids, the diffraction spectrum of this arrangement including a reflection peak of the first order in the range of wavelengths ranging from 250 nm to 1800 nm, preferably from 250 nm to 400 nm, —at least one absorber, said absorber being a molecule having an absorption spectrum in the UV-near IR domain (100 nm-3000 nm) whose mass extinction coefficient ε1% is greater than or equal to 160 $g^{-1} \cdot 100 \, mL \cdot cm^{-1}$, and —at least one surfactant.

19 Claims, 3 Drawing Sheets

(56) References Cited

OTHER PUBLICATIONS

French Preliminary Search Report dated Sep. 16. 2016 in Patent Application No. FR 1563419 (with English translation of categories of cited documents), 3 pages
Shin-Hyun Kim, et al. "Patterned Colloidal Photonic Domes and Balls Derived from Viscous Photocurable Suspensions" Advanced Materials, vol. 20, 2008, pp. 3211-3217.
"Process for Producing 3-Aminocyclohex-2-en-1-ylidene Compounds" ip.com, Jan. 25, 2013, pp. 1-41 and cover page.
F. J. Wang, et al., "Effects of Fabrication Conditions on the Characteristics of Etanidazole Spray-Dried Microspheres" Journal of Microencapsulation, vol. 19, No. 4, 2002, 495-510 and cover page.
Wang Duoren, "Modern Daily Chemical Products", Metallurgical Industry Press, Mar. 31, 2000, pp. 392-396 (with Partial English Translation).
Zheng Shuilin et al., "Non-metallic Mineral Processing and Application Manual", Metallurgical Industry Press, May 31, 2005, p. 341 (with English Translation).

\* cited by examiner

COMPOSITION COMPRISING PHOTONIC PARTICLES, AT LEAST ONE ABSORBER AND AT LEAST ONE SURFACTANT

The invention relates to a composition, especially a cosmetic composition and particularly a photoprotective composition and a treatment method for keratin substances, particularly the skin and its appendages, using said composition.

Current photoprotective compositions use combinations of different filtration agents, particularly soluble or insoluble organic filters. The absorption spectrum for each of these filters is rarely broad enough to cover the entire UV spectrum, and combinations are necessary.

Moreover, a great number of soluble organic filters may pose compatibility problems with the usual ingredients for compositions that contain them, especially because of interactions with other organic filters or with active molecules such as antioxidants or vitamins, and they may not have entirely satisfactory photostability. Many patents attempt to solve this problem, which shows just how recurrent it is.

Therefore a need remains to obtain compositions comprising UV filters that can cover the UVA and/or UVB spectrum, be perfectly harmless, environmentally inert, photostable and non-photoreactive, not causing compatibility problems with other component parts of the compositions that contain them, not negatively changing the mechanical properties of the packaging materials, not releasing nanoparticles, and transparent in visible light.

In a surprising manner, the inventors have observed that adding a quantity of photonic particles to a composition comprising at least one absorber amplifies the UV filtration performance and especially improves the SPF index.

From a sensorial point of view, the photonic particles also reduce the sticky feel due to the water-soluble UV filter. What is more, their fast sedimentation rate produces a very clean phase separation between the liquid phase and the aqueous phase, thereby retaining the transparent liquid phase.

The invention relates, according to a first feature, to a composition, especially a cosmetic composition, particularly a cosmetic photoprotective composition, comprising at least:
photonic particles having an average size comprised from 0.5 µm to 100 µm and each including a diffracting arrangement of monodisperse nanoparticles or voids, the diffraction spectrum of this arrangement including a reflection peak of the first order in the range of wavelengths ranging from 250 nm to 1800 nm, preferably from 250 nm to 400 nm,
at least one absorber, said absorber being a molecule having an absorption spectrum in the UV-near IR domain (100 nm-3000 nm) whose mass extinction coefficient $\varepsilon_{1\%}$ is greater than or equal to 160 g$^{-1}$·100 mL·cm$^{-1}$, and
at least one surfactant.

In the sense of the invention, "diffracting arrangement" is denoted by a set of particles or voids that diffract the incident light so as to filter the UV and/or produce a colour and/or change the spectral reflectance, depending on the application.

The presence of a reflection peak of the first order in the range of wavelengths ranging from 250 nm to 1800 nm means that the arrangement diffracts light radiation with an order of interference equal to 1 of at least one wavelength of between 250 nm and 1800 nm, thereby producing at least partial reflection thereof.

Such a reflection peak of the first order in UV implies that the reflection peaks for the following orders are at the shorter wavelengths, therefore outside the visible. This makes the arrangement colourless and facilitates obtaining a colourless composition, which is preferable in the scope of an application as a sunscreen filter.

According to another of its features, the invention relates to a method of preparing the composition according to the invention, including a step of dispersing in a cosmetically acceptable medium photonic particles according to the invention, at least one absorber and at least one wetting agent.

According to another of its features, the invention relates to a photoprotective cosmetic composition comprising, in a physiologically acceptable medium, a composition according to the invention as defined above.

The photoprotective cosmetic composition according to the invention is particularly suited to the use of a non-therapeutic photoprotection method for keratin substances.

The photoprotective cosmetic composition according to the invention has for example an SPF index of at least 5, or at least 10, better 15, best at least 30, 45 or 60. The SPF (Sunscreen Protection Factor) is defined in the article *A new substrate to measure sunscreen protection factors throughout the ultraviolet spectrum*, J. Soc. Cosmet. Chem., 40, 127-133 (May/June 1989).

The formulation of the photoprotective cosmetic composition is for example chosen such that the composition has a transmission factor less than or equal to 70%, 60%, 50%, 40%, 30%, 20%, 10%, 5% or best 1%, for at least one wavelength in the range 250-400 nm, better for the entirety of this range. The filtration is better when the transmission factor is low, in the range 250-400 nm.

According to another of its features, the invention relates to a non-therapeutic photoprotection method for keratin substances against solar UV radiation, comprising a step of applying a cosmetic composition according to the invention to said keratin substances.

The invention also relates to a process for colouring and/or bleaching keratin substances, and a method for changing the spectral reflectance of keratin substances, each of these methods comprising a step of applying a cosmetic composition according to the invention to said keratin substances.

The invention also relates to a non-therapeutic cosmetic process for limiting the darkening of the skin and/or improving the colour and/or uniformity of the complexion, comprising a step of applying a cosmetic composition according to the invention to skin.

The invention also relates to a non-therapeutic cosmetic method for preventing and/or treating the signs of ageing of a keratin substance, comprising a step of applying a cosmetic composition according to the invention to the surface of said keratin substance.

Photonic Particles

Figure 1:
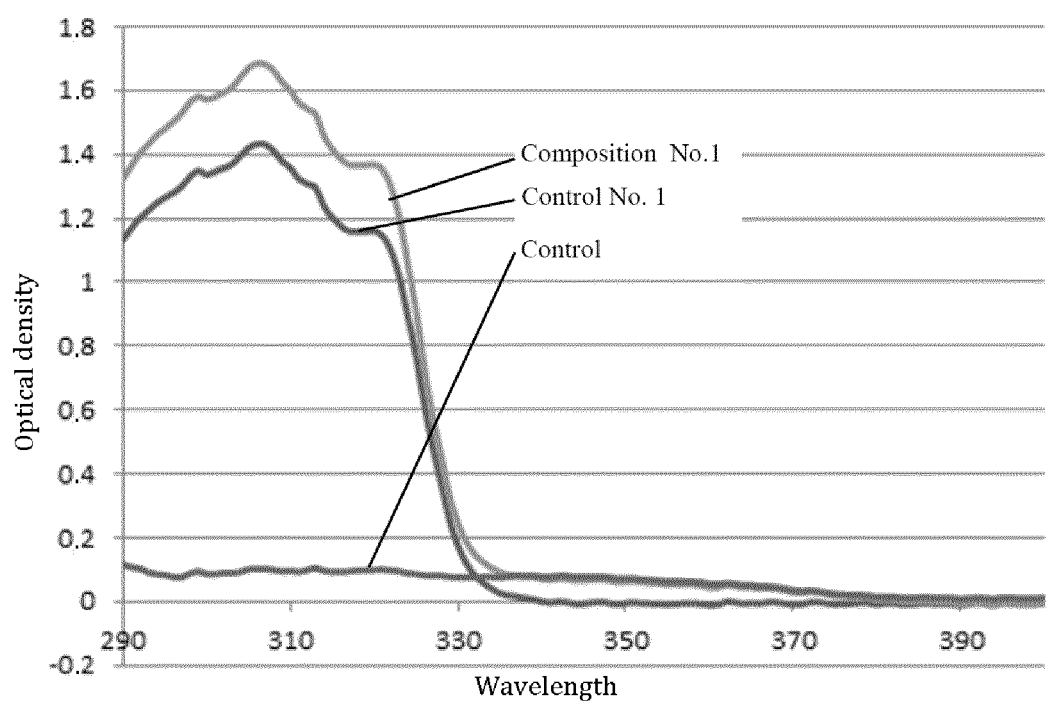
FIG. 1 represents an optical density curve for composition no. 1 and control composition no. 1 from the examples.

The photonic particles are, in the scope of the invention, also called opals.

According to one embodiment, the photonic particles are present in the composition in the form of an aqueous or oily dispersion.

The photonic particles may have a form factor less than 2, especially less than 1.75. The form factor denotes, when the particle is oblong, the ratio of its longest lengthwise dimension to its largest crosswise dimension. The photonic particles may be approximately spherical, with a form factor taken as equal to 1.

A form factor less than 2 may present an advantage in terms of surface coverage, with respect to flat particles that may be superimposed.

The mean size of photonic particles is comprised from 0.5 µm to 100 µm, preferably from 1 µm to 40 µm, advantageously from 5 µm to 25 µm, preferentially from 5 µm to 20 µm, even from 5 µm to 15 µm.

The term "mean size" denotes the statistical particle size dimension for half the population, referred to as D (0.5).

The photonic particles according to the invention may include solid or hollow nanoparticles aggregated without a matrix or aggregated or dispersed within any type of matrix, for example dispersed in a thermo-, electro- or photocrosslinkable matrix.

The weight content of photonic particles is preferably between 0.1% and 50%, preferentially between 0.5% and 10% by weight, relative to the total weight of the composition, before application. The photonic particles according to the invention may be, depending on the variants, qualified direct, inverse or pseudo-inverse opals as described below.

The photonic particles may be colourless.
The photonic particles may be solid or hollow.
Direct Opals The "direct opal" photonic particles use an arrangement of solid, optionally composite nanoparticles.

The photonic particles may include aggregated nanoparticles, preferably without a matrix.

A first manufacturing method for such particles, may, as described in the publication by S-H Kim et al, JACS, 2006, 128, 10897-10904, include a step of obtaining a water-in-oil emulsion, the aqueous phase including monodisperse nanoparticles, followed by a step of obtaining photonic particles including a step of microwave radiation of the emulsion obtained previously.

A second manufacturing method may, as described in the publication by S-M Yang in Langmuir 2005, 21, 10416-10421, include a step of aggregating $SiO_2$ or polystyrene (PS) nanoparticles in an electrospray.

The "direct opal" photonic particles may also be obtained by a process such as described in the publication "Ordered macroporous titania photonic balls by micrometer-scale spherical assembly templating" by Li et al, J. Mater. Chem., 2005, 15, 2551-2556.

The "direct opal" photonic particles may also be obtained by an atomization method.

According to this method, the particles to be atomized are first dispersed in a water-based medium or in a homogeneous water/solvent mixture, where the solvent is miscible with water, such as for example an alcohol such as ethanol. The particle concentration may be from 5% to 70% by weight. The resulting dispersion is added to an atomiser, such as for example NIRO MINOR PRODUCTION, the injection flow rate (in the case of this device) may be between 1000 and 10000 g/h, preferably between 2000 and 8000 g/h. The speed of rotation of the turbine is very high, preferably between 25000 and 45000 rpm. The atomization temperature may be comprised between 100 and 500° C. and preferably between 200 and 350° C.

The "direct opal" photonic particles may also include nanoparticles aggregated within a matrix, in contact with each other, or dispersed within a matrix.

Several methods, as well as the aforementioned methods, may be suitable for producing these photonic particles, especially the method of aggregating $SiO_2$ particles in a silicon matrix, described in the application US2003/0148088.

A second method may, as described in the publication by D. Pine in Langmuir 2005, 21, 6669-6674, include a step of aggregating from an emulsion of PMMA nanoparticles.

The "direct opal" photonic particles may include nanoparticles dispersed in a photo-, electro- or thermo-crosslinkable organic matrix.

The value of using a photocrosslinkable, electrocrosslinkable, or thermocrosslinkable organic matrix, especially a photocrosslinkable or thermocrosslinkable matrix, lies in the possibility of playing on the distance between the nanoparticles contained in the matrix to make the optical properties of the photonic particle vary. This distance may be a function of the weight fraction of nanoparticles dispersed in the organic matrix, before photo-, electro- or thermocrosslinking, especially before photo- or thermocrosslinking. Said weight fraction is equal to the weight ratio of the nanoparticles/weight of the matrix before thermo-, electro- or photocrosslinking.

According to a preferred embodiment of the invention, this weight fraction of nanoparticles is between 1 and 90% and preferably between 5 and 60%.

This type of photonic particle may be obtained by several methods by emulsification, for example those methods described in the publication by S-H Kim et al. Adv. Mater. 2008, 9999, 1-7 which uses silica particles dispersed in a photocrosslinkable ETPTA resin (ethoxylated trimethylolpropane triacrylate) that can be photopolymerized under UV or in the publication "Ordered macroporous titania photonic balls by micrometer-scale spherical assembly templating" by Li et al, J. Mater. Chem., 2005, 15, 2551-2556.

In some examples, the photonic particles are constituted of aggregated silica nanoparticles, without a matrix.

Inverse Opals

The "inverse opal" photonic particles include holes instead of nanoparticles.

They may be obtained from direct opals after destruction, for example by calcination or acid hydrolysis, for example with 5% hydrofluoric acid, of nanoparticles, thereby leaving empty spaces in the place of all or part of the nanoparticles. The destruction step may optionally cause a size reduction in the nanoparticle footprint within the matrix, ranging up to 50%.

Direct opals made of organic nanoparticles and an inorganic matrix may be calcinated (500 to 1000° C.).

Acid hydrolysis, with for example a hydrofluoric acid solution, may be done on opals based on inorganic nanoparticles and an organic matrix.

For inverse opals, the ratio of the volume occupied by the nanoparticles/volume occupied by the matrix (organic or precursor of the inorganic matrix) may be varied from 99/1 to 80/20, which will vary the surface porosity of the inverse opals. Such a variation is shown in the publication by D. Pine, F. Lange, Langmuir 2005, 21, 6669-6674.

The inverse opals may be produced by the aforementioned methods for direct opals including aggregated or dispersed nanoparticles within a matrix, followed by a step of destroying nanoparticles, for example by calcination or acid hydrolysis, such as for example described in the following publications:

A. Stein: Chem. Mater. 2002, 14, 3305-3315 where the opals are made from monodisperse particles in zirconium acetate matrices for ZrO articles, from Ti propoxide for opals made of $TiO_2$, or from tetramethoxysilane (TMOS) for opals made of silica. After calcination the PS particles leave behind voids. The final material is then milled to produce the opal powder.

D. Pine, F F Lange: Langmuir, Vol 21, 15, 2005, 6669-6674 which describes how to make spherical opals by an emulsification method before a step of calcinating the PMMA particles. Opal porosity is controlled by the Ti alkoxide/PMMA particle level ratio.

F F Lange Colloid Polym. Sci. (2003) 282, 7-13 which describes the emulsification of PMMA particles in the presence of Ti butoxide then the calcination of PMMA particles.

By nature, inverse opals have no additional treatment of the porous materials whose optical properties will vary as a function of the medium, that may fill the holes in the opals.

To guarantee the optical properties in any medium, photonic particles with inverse opal structure may be coated and made impervious to the medium in which they are submerged.

This coating can for example be made of polymers or waxes.

Several methods are possible:
- spray drying or atomization: the principle is to solubilize or disperse (for latex) the material that will coat the photonic particles in a volatile solvent with an evaporation point less than or equal to 100° C. (ethanol, acetone, isopropanol, water, etc. or mixtures thereof). The entirety is sprayed in a chamber brought to a temperature that allows the solvent or mixture to evaporate to lead to the coating material being deposited on the particles. The articles are carried, by an air flow, to a container at room temperature, to be collected there. For example, mention may be made of the publication "Effects of fabrication conditions on the characteristics of etamidazole spray dried microspheres": Wang et Al, J. Microencapsulation, 2002, vol. 19, No. 4, 495-510.
- fluidized air bed: the fluidized air bed is a method used frequently for drying and making granules. A moderate air flow is introduced from the floor of the reactor. The suspension sprayed by an atomiser in the production chamber makes the suspension particles larger; they then fall to the floor once they cannot be carried by the air flow.

In a non-limiting manner, the materials for coating the particles may be chosen from:
- waxes and fatty substances with a melting point greater than 45° C. especially carnauba wax, beeswax, stearyl stearate, polyethylene wax, DI 18/22 adipate, pentaerythrityl tetrastearate, tetracontanyl stearate, diocta-decyl carbonate,
- cellulose and cellulose derivatives, especially ethylcellulose, hydroxypropyl cellulose, hydroxypropylmethyl cellulose, hydroxybutyl cellulose, polymers sold under the brand Ethocel®,
- polycaprolactone having a molecular weight ranging from 10000 to 80000 g/mol,
- polylactic acid (PLA) and polylactic acid-glycolic acid (PLAGA) ratio 90/10 to 50/50,
- polyvinyl alcohol,
- polyvinylpyrrolidone vinyl acetate copolymers, and
- acrylic acid and methyl methacrylate copolymers sold under the brand Eudragit® L100, The mass ratio between the core of the photonic particle and the resulting shell may be between 99.9/0.1 and 80/20, and preferably between 99/1 and 90/10.

Pseudo-Inverse Opals

"Pseudo-inverse opal" photonic particles include hollow nanoparticles aggregated without a matrix or aggregated or dispersed within any type of matrix, for example dispersed in a thermo-, electro-, or photocrosslinkable matrix.

Making direct opals, also called "pseudo-inverse opals", from hollow nanoparticles has the advantages of amplifying the optical effects by a higher index difference compared with direct opals that do not use hollow nanoparticles, and of offering zero porosity compared with uncoated inverse opals, whose optical properties depend on the medium in which they are dispersed.

The hollow nanoparticles may be as described below.

Janus Photonic Particles

Photonic particles may be Janus particles, i.e. include at least one other nanoparticle diffracting arrangement, or at least two other diffracting arrangements, the arrangements each having clean optical properties, especially different diffraction spectra.

In a first embodiment, an arrangement may include solid nanoparticles and another arrangement may include solid or hollow nanoparticles.

As a variant, an arrangement may include hollow nanoparticles and another arrangement may include hollow nanoparticles.

When the particles include several arrangements, each arrangement may cover for example one part of the UV spectrum, so as to obtain broader photoprotection.

Photonic particles including several diffraction arrangements may be obtained as taught in the publication by S-H Kim et al. Adv. Mater. 2008, 9999, 1-7 or the publication "Patterned colloidal photonic domes and balls derived from viscous photocurable suspensions" by Kim et al., Adv. Mater. 2008, 20, 3211-3217.

When the photonic particles are used at least in part for their colour properties, particularly for homogenization of the complexion, the arrangements of nanoparticles, when lit by white light, may produce different respective colours; the arrangements may especially produce red, green and/or blue, thereby allowing the production of a large number of tones and particularly white by additive synthesis of reflected light.

An arrangement presents a red reflected colour, for example, when the reflectance in the visible spectrum is at least 50% in the wavelength ranging from 620 to 700 nm, for an observation angle varying between 30 and 150°. For green, the wavelength considered ranges from 490 to 550 nm and for blue from 410 to 490 nm. The arrangements may diffract light through different respective areas of the photonic particle, for example two opposite areas, for example two hemispherical diametrically opposed areas in the case of a spherical photonic particle.

One of the arrangements may have a diffraction spectrum with at least one reflection peak of the first order in the wavelength range from 250 to 400 nm and another arrangement may have a diffraction spectrum with at least one reflection peak of the first order in the wavelength range from 250 to 400 nm or 400 to 700 nm.

Mixture of Photonic Particles

The composition according to the invention may include a single type of photonic particle or a mixture of at least two different types of photonic particle for example having reflection peaks, especially of the first order, centred on different wavelengths, located in the visible, UV or near-IR region.

The composition may for example include a mixture of a type of photonic particle including filled nanoparticles and another type of photonic particles including nanoparticles that may be solid or hollow.

The composition may for example include a mixture of a type of photonic particle including hollow nanoparticles and another type of photonic particle including nanoparticles that may be hollow.

The composition may for example include a mixture of a type of photonic particle including a thermo-, electro- or photocrosslinkable matrix and another type of photonic particle not including a thermo-, electro- or photocrosslinkable matrix.

Nanoparticles

The nanoparticles that form the photonic particles may have a mean size comprised from 100 nm to 500 nm, preferably from 100 nm to 400 nm.

The term "mean size" denotes the statistical particle size dimension for half the population, referred to as D (0.5).

The nanoparticles may be spherical.

The nanoparticles may be 15% monodisperse or better. The term "x % monodisperse" qualifies according to the invention particles whose mean size has a coefficient of variation CV less than or equal to x %.

The coefficient of variation CV is defined by the relation:

$$CV = s/D,$$

where s is the standard deviation of the particle size distribution, and

D is their mean size.

The mean size D and standard deviation s may be measured on 250 particles by analysis of an image obtained using a scanning electron microscope, for example the S-4 500 microscope from Hitachi. An image analysis software package may be used to facilitate this measurement, for example the Winroof® software package, sold by the company Mitani Corporation. Preferably, the coefficient of variation of the monodisperse nanoparticles is less than or equal to 10%, preferably less than or equal to 7%, even more preferably less than or equal to 5%, being for example approximately of the order of 3.5% or less.

The nanoparticles may be solid or hollow, organic or inorganic.

The nanoparticles may be a single material or composites.

When the monodisperse nanoparticles are composites, they may for example include a core and a shell made of different materials, for example organic and/or inorganic materials.

Inorganic Nanoparticles

The nanoparticles may include an inorganic compound, or be entirely inorganic.

When the nanoparticles are inorganic, they may for example include at least one oxide, especially a metal oxide, and chosen for example from silica, silica, iron, titanium, aluminium, chromium, zinc, copper, zirconium and cerium oxides and mixtures thereof. The nanoparticles may also include a metal, especially titanium, silver, gold, aluminium, zinc, iron, copper and mixtures and alloys thereof.

According to one embodiment, the nanoparticles comprise silica, at least one metal oxide, especially as described above, or a mixture of silica and at least one metal oxide, especially as described above.

Organic Nanoparticles

The nanoparticles may include an organic compound, or be entirely organic.

Among the materials that may be suitable for making organic nanoparticles, mention may be made of polymers, especially with carbon-based or silicon-based chains, for example polystyrene (PS), polymethyl methacrylate (PMMA), polyacrylamide (PAM), silicone polymers, NAD ("non-aqueous dispersions") such as for example rigid NAD that, as examples, are constituted of 96.7% methyl methacrylate and 3.3% ethylene glycol dimethacrylate crosslinked at 20% in isododecane, particle diameter: 141 nm (polydispersity Q=0.14) or 90% methyl methacrylate and 10% allyl methacrylate, particle diameter: 170 nm or 100% methyl dimethacrylate, particle diameter: 138 nm (polydispersity Q=0.15) or poly(methyl methacrylate/allyl methacrylate, polylactic acid (PLA), polylactic acid-glycolic acid (PLAGA), celluloses and their derivatives, polyurethane, polycaprolactone, latex form, chitin, composite chitin materials.

The glass transition temperature ($T_g$) of the organic nanoparticles may be greater than 40° C., and preferably greater than 60° C.

Hollow Nanoparticles

These nanoparticles include a core and a shell. The shell may be organic or inorganic.

The nanoparticle shell may for example be made of PS and the particles may for example be aggregated within an organic matrix.

The nanoparticle shell may for example be made of PS and the particles may for example be aggregated within an organic thermo-, electro- or photocrosslinkable matrix.

The core of these hollow nanoparticles may be constituted of air or a gas other than air to benefit from a different refraction index, for example $CO_2$, $N_2$, butane or isobutane.

The presence of air or another gas inside the hollow nanoparticles may make it possible to obtain a great difference in refraction index between the nanoparticles and the surrounding environment, which is favourable in terms of intensity of the diffraction peak.

When the nanoparticles are hollow, the difference in refraction index at a wavelength diffracted between the core and the shell may be greater than or equal to 0.4. Said diffracted wavelength may be between 250 and 800 nm, for example between 250 and 400 nm. When the nanoparticles are hollow, the ratio between a larger dimension of the core and a larger dimension of the nanoparticle may be between 0.5 and 0.8. When the nanoparticles are hollow, the core volume represents between 10 and 80%, preferably between 20 and 60%, of the total volume of the nanoparticle.

The thickness of the shell of hollow nanoparticles, taken as equal to half the difference of the largest dimension of the nanoparticle and the largest dimension of the core of the nanoparticle, may be between 50 and 200 nm, for example between 30 and 100 nm.

Among hollow nanoparticles that can be used, mention may be made of 280 nm nanoparticles from the company JSR SX866(B).

The shell of the nanoparticles may optionally include a sunscreen filter or a mixture of sunscreens.

Matrix

The photonic particles may include solid or hollow nanoparticles, aggregated or dispersed within any type of matrix, for example dispersed within a thermo-, electro- or photocrosslinkable matrix, or voids dispersed in any type of matrix, for example dispersed within a thermo-, electro- or photocrosslinkable matrix, such as the aforementioned.

The matrix may be organic or inorganic.

Among the organic matrices, mention may be made, in a non-limiting manner, of acrylic matrices: made of polymethyl methacrylate (PMMA) or polyacrylamide (PAM), matrices made of polyethylene terephthalate (PET), polystyrene (PS), polycaprolactone (PCL), polyvinyl acetate (PVA), polyvinylethyl acetate (PVEA), waxes with melting points greater than 65° C., for example greater than 75° C., and hardness greater than 5 MPa and preferably greater than 6 MPa.

Specifically, the matrix may be thermocrosslinkable, photocrosslinkable or electrocrosslinkable.

"Photocrosslinkable matrix" should be understood as a matrix whose crosslinking is caused and/or assisted by light radiation, especially UV radiation.

"Thermocrosslinkable matrix" should be understood as a matrix whose crosslinking is caused and/or assisted by providing heat, for example bringing the matrix to a temperature greater than 60° C.

"Electrocrosslinkable matrix" should be understood as a matrix whose crosslinking is caused and/or assisted by applying an electric field.

A matrix may be both thermo- and photocrosslinkable.

The photonic particles may include solid or hollow nanoparticles, dispersed within a thermo-, electro- or photocrosslinkable matrix or voids dispersed within a thermo-, electro- or photocrosslinkable matrix.

The thermo- or photocrosslinkable matrix may be organic.

Among the organic crosslinkable matrices, mention may be made in a non-limiting manner of:
  photocrosslinkable polymers such as ETPA (ethoxylated trimethylolpropanetriacrylate), PEGDA (polyethyleneglycol diacrylate), acrylic resins, PEG diacrylates, the materials described in FR 2 833 487,
  copolymers described in FR 2 848 428 that crosslink by polycycloaddition, PVA or PVEA and styrylpyridiniums having the following formula:

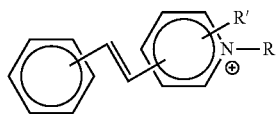

where R represents a hydrogen atom, an alkyl or hydroxyalkyl group, and R' represents a hydrogen atom or an alkyl group, reactive silicones described in patent FR 2 910 286, i.e.: polyorganosiloxanes including siloxane units having the formula:

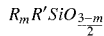

in which R is a monovalent, linear or cyclic hydrocarbon group including from 1 to 30 carbon atoms, m is 1 or 2 and R' is an unsaturated aliphatic hydrocarbon group including from 2 to 10 carbon atoms or a cyclic hydrocarbon group including from 5 to 8 carbon atoms and/or polyorganosiloxanes including at least one alkylhydrogensiloxane unit having the formula:

where R is a monovalent, linear or cyclic hydrocarbon-based group including from 1 to 30 carbon atoms or a phenyl group and p is 1 or 2, and
  thermoplastic, thermocrosslinkable, electrocrosslinkable polymers.

The matrix may be crosslinked using chemical crosslinking, for example using succinimides as described in application WO 2007082061 A2. For photocrosslinkable matrices requiring a photoinitiator, the photoinitiator is chosen for example from the following list: DMPA (dimethoxy 2-phenylacetophenone), 2-benzyl-2-(dimethylamino)-1-[4-(4-morpholinophenyl]-1-butanone sold under the brand Irgacure® 369 by Ciba®, 4,4'-bis(diethylamino)benzophenone sold by Sigma-Aldrich®, 2-hydroxy-4'-(2-hydroxyethoxy)-2-methylpropiophenone sold by Sigma-Aldrich®, 2-benzyl-2-(dimethylamino)-4'-morpholinobutyrophenone sold by Sigma-Aldrich®, phenylbis(2,4,6-trimethylbenzoyl)-phosphine oxide sold by Sigma-Aldrich®, isopropyl-thioxanthone sold by Sigma-Aldrich®, and camphorolactone.

PEG diacrylates may for example crosslink using a photoinitiator such as camphorolactone.

Among inorganic matrices, mention may be made, as an example, of metal oxide matrices, especially $SiO_2$, $TiO_2$, $ZrO$, or $CaCO_3$ or $Si$ matrices.

Absorber

The composition according to the invention comprises at least one absorber, at a content comprised preferably from 0.01% to 60%, preferentially from 0.1% to 30%, by weight relative to the total weight of said composition.

"Absorber" is understood here to mean a substance used to absorb energy of any type of radiation, preferably a molecule having an absorption spectrum in the UV-near IR domain (100 nm-3000 nm) whose mass extinction coefficient $\varepsilon_{1\%}$ is greater than or equal to 160 $g^{-1} \cdot 100$ $mL \cdot cm^{-1}$.

The Beer-Lambert Law gives the absorbance of a solute (for example an absorber) as a function of its concentration:

$$A = \log I/I_0 = \varepsilon \cdot l \cdot c$$

in which: A is the absorbance,
  $I_0$ is the incident light intensity,
  I is the transmitted light intensity,
  $\varepsilon$ is the extinction coefficient (which depends on the wavelength),
  l is the measurement tank length, and
  c is the solute concentration.

If the solute concentration is in % (mass/volume), $\varepsilon$ is then expressed in $g^{-1} \cdot L \cdot cm^{-1}$ and called the mass extinction coefficient: $\varepsilon_{1\%}$.

The mass extinction coefficient, $\varepsilon_{1\%}$, is determined at the maximum absorbance wavelength of the solute.

Preferably, the absorber is chosen from the group constituted of:
  organic, soluble or insoluble, preferably water-soluble or water-dispersible UV filters,
  inorganic, preferably water-dispersible, UV filters,
  synthetic or natural colourants, such as tartrazine, phloridzin, quinoline, and carotenoids, such as for example lutein, asthaxantin, and beta-carotene,
  natural or synthetic polyphenols, derivatives thereof, and plant extracts comprising them,
  and mixtures thereof.

For the purposes of the present invention, "polyphenol derivative" is intended especially to mean the esters, glucosides and phosphates of polyphenols.

Among polyphenols, mention may mainly be made of phenol acids and derivatives thereof (chlorogenic acid), and flavonoids, which represent the main sub-group of polyphenols.

Among flavonoids, mention may especially be made of chalcones, hydroxylated chalcones and derivatives thereof, such as phloretin, neohesperidin, phloridzin and aspalathin; flavanones, such as hesperetin and naringin; flavonols, such as quercetin and rutin; flavanols, such as catechin and EGCG; flavones, such as apigenin; and anthocyans.

Mention may also be made of tannins, such as ellagic tannins especially.

The polyphenols may especially derive from plant extracts chosen from green tea, apple, hops, guava or cacao extracts, or from wood, such as chestnut, oak, horse chestnut or hazel, from extracts of Rock Tea or pomegranate extracts, Japanese knotweed extracts (*Fallopia japonica*, also known as *Polygonum cupistadum* or *Reynoutria japonica*), grape extracts, such as for example those from the grapevine species *Vitis vinifera*, blackberry extracts, wine, peanut extracts, and extracts from the following families of plants: Vitaceae, Myrtaceae, Dipterocarpaceae, Cyperaceae, Gnetaceae, Fabaceae, Pinaceae, Polygonaceae, Moraceae, Fagaceae, Liliaceae, etc.

The polyphenols are especially baicalin, apigenin, leontopodic acid, ferulic acid, ellagic acid, resveratrol, myricetin, and dihydroquercetin.

According to a preferred embodiment, the absorber is an organic, water-soluble UV filter, preferably a mixture of at least two organic, water-soluble UV filters, advantageously a mixture of at least one organic, water-soluble UVA filter and at least one organic, water-soluble UVB filter.

The organic, water-soluble UV filters are especially chosen from the following families:

Water-Soluble Filters that can Absorb UV from 320 to 400 nm (UVA)

Terephthalylidene dicamphor sulfonic acid manufactured under the name Mexoryl SX by Chimex.

Bis-benzazolyl derivatives as described in patents EP 669 323 and U.S. Pat. No. 2,463,264, and more particularly the compound disodium phenyldibenzimidazole tetrasulfonate sold under the trade name Neo Heliopan AP by Haarmann & Reimer, The preferred filter is terephthalylidene dicamphor acid sulfonic acid.

Water-Soluble Filters that can Absorb UV from 280 to 320 nm (UVB)

p-Aminobenzoic Acid (PABA) Derivatives

PABA,

Glyceryl PABA and

PEG-25 PABA sold under the name Uvinul P25 by BASF,

Phenylbenzimidazole sulfonic acid sold especially under the trade name Eusolex 232 by Merck, Ferulic acid, Salicylic acid, DEA methoxycinnamate, Benzylidene camphor sulfonic acid manufactured under the name Mexoryl SL by Chimex, Camphorbenzalkonium methosulfate manufactured under the name Mexoryl SO by Chimex, and The preferred water-soluble filter is phenylbenzimidazole sulfonic acid.

Mixed UVA and UVB Water-Soluble Screening Agents

Benzophenone Derivatives Comprising at Least One Sulfonic Substituent

Benzophenone-4 sold under the trade name Uvinul MS40 by BASF,

Benzophenone-5, and

Benzophenone-9.

When the absorber is an organic UV filter of the sulfonic acid type, it is preferably combined with a quantity of an organic base, such as an alkanolamine, so as to make it water soluble.

"Alkanolamine" is understood to mean a $C_2$-$C_{10}$ compound comprising at least one primary, secondary or tertiary amine function, and at least one alcohol function, generally primary.

As appropriate alkanolamines, mention may be made of tromethanine and triethanolamine.

Preferably, the composition according to the invention comprises the filter combination of terephthalylidene dicamphor sulfonic acid and phenylbenzimidazole sulfonic acid.

Surfactants

The composition according to the invention also comprises at least one surfactant, at a content preferably comprised from 0.5% to 10% by weight relative to the total weight of the composition, said surfactant having preferably a HLB greater than 7, said surfactant being preferentially non-ionic.

It has been noticed that the surfactants are particularly interesting for providing an homogeneous dispersion of the photonic particles. It permits the prevention of any aggregation phenomenon of these particles. They also contribute to a better efficiency and better cosmetic properties of these compositions, which are less white, more transparent and more homogeneous when applied to the skin. It permits to obtain a better softness of the treated skins.

The term "HLB" is well known to those skilled in the art, and denotes the hydrophilic-lipophilic balance of a surfactant at 25° C. in the Griffin sense.

The term "hydrophilic-lipophilic balance (HLB)" is intended to mean the equilibrium between the size and the strength of the hydrophilic group and the size and the strength of the lipophilic group of the surfactant. This HLB value according to Griffin is defined in J. Soc. Cosm. Chem. 1954 (volume 5), pages 249-256.

The surfactant(s) having an HLB less than or equal to 7 may be ionic or non-ionic. Use may especially be made of the surfactants having an HLB less than or equal to 7 which are mentioned in the reference handbook McCutcheons Emulsifiers & Detergents, International Edition from 1998 et seq.

Reference may also be made to Kirk-Othmer's Encyclopedia of Chemical Technology, volume 22, pp. 333-432, 3rd edition, 1979, Wiley, for the definition of the emulsifying properties and functions of surfactants, in particular pp. 347-377 of this reference, for non-ionic surfactants.

For ionic surfactants, the HLB of surfactants in the form of individual molecules may be calculated by applying the Davies formula. According to this formula, the HLB is derived by adding the hydrophilic/hydrophobic contributions provided by the surfactant's structural components:

$$HLB=\Sigma(\text{contributions from hydrophilic groups})-\Sigma(\text{contributions from hydrophobic groups})+7.$$

The Griffin formula is generally used for non-ionic surfactants and the Davis formula is used for ionic surfactants.

The HLB are defined at room temperature.

Advantageously, the composition according to the invention comprises at least one surfactant with HLB greater than 7 and preferably less than 40, preferably greater than 10 and less than 20, for example from 7 to 20.

According to one embodiment, the composition according to the invention comprises one or more surfactants with HLB greater than 7, chosen from non-ionic, amphoteric and anionic surfactants.

The non-ionic surfactants are more especially chosen from:
  fatty acid esters, especially $C_8$-$C_{24}$ fatty acid esters, and sugars and fatty alcohol ethers of sugars,
  oxyalkylenated glycerol ethers, in particular oxyethylenated and/or oxypropylenated glycerol ethers, that may comprise from 5 to 100 oxyethylene and/or oxypropylene units, preferably from 10 to 80 oxyethylene and/or oxypropylene units;
  oxyalkylenated alcohols, especially oxyethylenated and/or oxypropylenated alcohols, that may comprise from 5 to 100 ethylene and/or propylene oxide units, preferably from 10 to 100 ethylene oxide units, especially fatty alcohols, especially $C_8$-$C_{24}$ fatty alcohols, and preferably $C_{12}$-$C_{18}$ fatty alcohols, ethoxylated such as stearyl alcohol ethoxylated with 20 ethylene oxide units (CTFA name "Steareth-20") such as BRIJ 78 sold by Uniqema, cetyl alcohol ethoxylated with 20 ethylene oxide units (CTFA name "Ceteth-20"), cetearyl alcohol ethoxylated with 30 ethylene oxide units (CTFA name "Ceteareth-30") and the mixture of $C_{12}$-$C_{15}$ fatty alcohols comprising 7 ethylene oxide units (CTFA name "$C_{12-15}$ Pareth-7") such as that sold as NEODOL 25-7® by Shell Chemicals;
  fatty acid esters, especially $C_8$-$C_{24}$ fatty acid esters, and preferably $C_{16}$-$C_{22}$ fatty acid esters, and of polyethylene glycol (or PEG) (that may comprise from 5 to 100 ethylene oxide units, preferably from 10 to 80 ethylene oxide units), such as PEG-50 stearate and PEG-40 monostearate sold as MYRJ 52P® by Uniqema, or also PEG-75 stearate;
  esters of a fatty acid, especially a $C_8$-$C_{24}$ and preferably $C_{16}$-$C_{22}$ fatty acid, and of oxyalkylenated glycerol ethers, which are especially oxyethylenated and/or oxypropylenated (which may comprise from 5 to 100 oxyethylene and/or oxypropylene units), for instance glyceryl monostearate polyoxyethylenated with 200 oxyethylene units, sold under the name Simulsol 220 TM® by the company SEPPIC; glyceryl stearate polyoxyethylenated with 30 oxyethylene units, for instance the product Tagat S® sold by the company Goldschmidt, glyceryl oleate polyoxyethylenated with 30 oxyethylene units, for instance the product Tagat O® sold by the company Goldschmidt, glyceryl cocoate polyoxyethylenated with 30 oxyethylene units, for instance the product Varionic LI 13® sold by the company Sherex, glyceryl isostearate polyoxyethylenated with 30 oxyethylene units, for instance the product Tagat L® sold by the company Goldschmidt, and glyceryl laurate polyoxyethylenated with 30 oxyethylene units, for instance the product Tagat I® from the company Goldschmidt;
  esters of a fatty acid, especially a $C_8$-$C_{24}$ and preferably $C_{16}$-$C_{22}$ fatty acid, and of advantageously oxyalkylenated sorbitol, which are especially oxyethylenated and/or oxypropylenated (which may comprise from 5 to 100 oxyethylene and/or oxypropylene units), such as polysorbate 60 especially sold under the name Tween 60® by the company Uniqema and more particularly sorbitan monolaurate oxyethylenated with 20 moles of ethylene oxide (INCI name=Polysorbate-20) especially sold under the name Tween 20® by the company Uniqema;
  silicone surfactants,
  copolymers of propylene oxide and ethylene oxide, also known as EO/PO polycondensates;
  and mixtures thereof.

The fatty acid and sugar esters that may be used as non-ionic surfactant above may preferably be solid at a temperature of less than or equal to 45° C. and may be chosen in particular from the group comprising esters or mixtures of esters of $C_8$-$C_{22}$ fatty acids and of sucrose, maltose, glucose or fructose, and esters or mixtures of esters of $C_{14}$-$C_{22}$ fatty acids and of methylglucose.

As examples of esters or mixtures of esters of fatty acid and of sucrose, maltose, glucose or fructose, mention may be made of sucrose monostearate, sucrose distearate and sucrose tristearate and mixtures thereof, such as the products sold by the company Croda under the name Crodesta F50, F70, F110 and F160; and an example of esters or mixtures of esters of fatty acid and of methylglucose that may be mentioned is methylglucose-polyglyceryl-3 distearate, sold by the company Goldschmidt under the name Tego-Care 450. Mention may also be made of glucose or maltose monoesters such as methyl-o-hexadecanoyl-6-D-glucoside and o-hexadecanoyl-6-D-maltoside.

The fatty alcohol ethers, especially $C_8$-$C_{24}$, and of sugars, that may be used as non-ionic surfactant above may be solid at a temperature of less than or equal to 45° C. and may be chosen especially from the group comprising ethers or mixtures of ethers of $C_8$-$C_{22}$ fatty alcohols and of glucose, maltose, sucrose or fructose, and ethers or mixtures of ethers of a $C_{14}$-$C_{22}$ fatty alcohol and of methylglucose. These are in particular alkylpolyglucosides.

The $C_8$-$C_{22}$ or $C_{14}$-$C_{22}$ fatty alcohols forming the fatty acid unit of the ethers that may be used in the nanoemulsion of the invention comprise a saturated or unsaturated linear alkyl chain containing, respectively, from 8 to 22 or from 14 to 22 carbon atoms. The fatty acid unit of the ethers may be chosen in particular from decyl, cetyl, behenyl, arachidyl, stearyl, palmityl, myristyl, lauryl, capryl and hexadecanoyl units, and mixtures thereof such as cetearyl.

As examples of fatty alkyl ethers of sugars, mention may be made of ($C_8$-$C_{22}$)alkylpolyglucosides such as decyl glucoside and lauryl glucoside sold, for example, by the company Henkel under the respective names Plantaren 2000 and Plantaren 1200, cetostearyl glucoside optionally as a mixture with cetostearyl alcohol, sold, for example, under the name Montanov 68 by the company SEPPIC, under the name Tego-Care CG90 by the company Goldschmidt and under the name Emulgade KE3302 by the company Henkel, and also arachidyl glucoside, for example in the form of a mixture of arachidyl alcohol and behenyl alcohol and arachidyl glucoside, sold under the name Montanov 202 by the company SEPPIC.

The surfactant used is more particularly sucrose monostearate, sucrose distearate or sucrose tristearate and mixtures thereof, polyglyceryl-3 methylglucose distearate and ($C_8$-$C_{22}$)alkylpolyglucosides.

The fatty acid esters of glycerol that may be used as non-ionic surfactant above, which are solid at a temperature of less than or equal to 45° C., may be chosen in particular from the group comprising esters formed from at least one acid comprising a saturated linear alkyl chain containing from 12 to 22 carbon atoms and from 1 to 12 glycerol units. One or more of these fatty acid esters of glycerol may be used in the present invention.

These esters may be chosen in particular from glyceryl stearates, behenates, arachidates and palmitates, and mixtures thereof. Glyceryl stearates and palmitates are preferably used.

As examples of surfactants that may be used in the present invention, mention may be made of decaglyceryl monostearate, distearate, tristearate and pentastearate (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1 S, 2 S, 3 S and 5 S by the company Nikko, and diglyceryl monostearate (CTFA name: polyglyceryl-2 stearate), such as the product sold by the company Nikko under the name Nikkol DGMS.

The fatty acid esters of sorbitan that may be used as non-ionic surfactant above may be chosen from the group comprising esters of $C_{16}$-$C_{22}$ fatty acids and of sorbitan and oxyethylenated esters of $C_{16}$-$C_{22}$ fatty acids and of sorbitan. They are formed from at least one fatty acid comprising at least one saturated linear alkyl chain containing, respectively, from 16 to 22 carbon atoms and from sorbitol or ethoxylated sorbitol. The oxyethylenated esters generally comprise from 2 to 100 ethylene glycol units and preferably from 4 to 40 ethylene oxide (EO) units.

These esters may be chosen in particular from stearates, behenates, arachidates and palmitates, and mixtures thereof. Stearates and palmitates are preferably used.

As examples of the above non-ionic surfactant that may be used in the present invention, mention may be made of sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65.

EO/PO polycondensates are more particularly copolymers formed from polyethylene glycol and polypropylene glycol blocks, for instance polyethylene glycol/polypropylene glycol/polyethylene glycol triblock polycondensates. These triblock polycondensates have, for example, the following chemical structure:

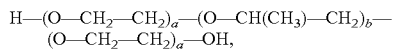

in which formula a ranges from 2 to 120 and b ranges from 1 to 100.

The EO/PO polycondensates preferably have a weight-average molecular weight ranging from 1000 to 15 000 and better still ranging from 2000 to 13 000. Advantageously, the said EO/PO polycondensates have a cloud point, at 10 g/l in distilled water, of greater than or equal to 20° C., preferably of greater than or equal to 60° C. The cloud point is measured according to the standard ISO 1065. Mention may be made, as EO/PO polycondensate that can be used according to the invention, of the polyethylene glycol/polypropylene glycol/polyethylene glycol triblock polycondensates sold under the Synperonic® names, such as Synperonic PE/L44® and Synperonic PE/F127®, by ICI.

The amphoteric surfactants may be chosen, for example, from betaines, N-alkylamido betaines and derivatives thereof, glycine derivatives, sultaines, alkyl polyaminocarboxylates, alkylamphoacetates, and mixtures thereof.

Betaines that may be mentioned are for instance cocoyl betaine, such as the product sold under the name Dehyton AB-30® by the company Henkel, lauryl betaine, such as the product sold under the name Genagen KB® by the company Clariant, oxyethylenated (10 EO) lauryl betaine, such as the product sold under the name Lauryl Ether (10 EO) Betaine® by the company Shin Nihon Rica, or oxyethylenated (10 EO) stearyl betaine, such as the product sold under the name Stearyl Ether (10 EO) Betaine® by the company Shin Nihon Rica.

Among the N-alkylamido betaines and derivatives thereof, examples that may be mentioned include the cocamidopropyl betaine sold under the name Lebon 2000 HG® by the company Sanyo or sold under the name Empigen BB® by the company Albright & Wilson, or the lauramidopropyl betaine sold under the name Rewoteric AMB12P® by the company Witco.

As glycine derivatives, mention may be made of sodium N-cocoylglycinate sold under the name Amilite GCS-12® by the company Ajinomoto.

Mention may be made, as sultaines, of cocoylamidopropyl hydroxysulfobetaine, sold under the name Crosultaine C-50® by Croda.

Alkyl polyaminocarboxylates (APACs) that may be mentioned include sodium cocoylpolyaminocarboxylate, sold under the names Ampholak 7 CX/C® and Ampholak 7 CX® by the company Akzo Nobel, sodium stearylpolyamidocarboxylate, sold under the name Ampholak 7 TX/C by the company Akzo Nobel, or sodium carboxymethyl oleyl polypropylamine, sold under the name Ampholak XO7/C® by the company Akzo Nobel.

Alkylamphoacetates that may be mentioned include compounds with the following general formula (II):

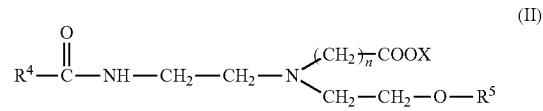

in which:
R4 represents a saturated or unsaturated hydrocarbon substituent, such as a fatty acid unit,
R5 represents a hydrogen atom or the group —(CH2)m-COOY,
X and Y represent, independently or simultaneously, a hydrogen atom or a monovalent cation, especially a metal cation and particularly an alkaline cation such as sodium,
n and m are two integers that can be, independently or simultaneously, 1 or 2.

Amphoteric surfactants having formula (II) above that enter particularly well into the scope of this invention are those having at least one, and preferably several, of the following characteristics: n and m are the same; R5 represents the group —(CH$_2$)m-COOY; X and Y are the same and represent preferably a monovalent metal cation, particularly sodium; R4 represents an alkyl substituent generally from $C_5$-$C_{20}$, especially $C_7$, $C_9$, $C_{11}$, $C_{13}$ or $C_{17}$, an unsaturated $C_{17}$ substituent, or even an alkyl substituent of a R4-COOH acid present in natural oils, such as coconut, copra, linseed, wheat germ or animal tallow.

As concrete examples of imidazoline amphoteric surfactants, mention may especially be made of those sold under the general trade name Miranol® by the company Rhodia Chimie, and those with the following CTFA names (CTFA Dictionary, 4th edition, 1991):
Disodium Caproamphodiacetate,
Disodium Caproamphodipropionate,
Disodium Caprylamphodiacetate,
Disodium Caprylamphodipropionate, Disodium Cocoamphodiacetate,
Disodium Cocoamphodipropionate,
Disodium Isostearoamphodiacetate,
Disodium Isostearoamphodipropionate,
Disodium Lauroamphodiacetate,
Disodium Lauroamphodipropionate,
Disodium Oleoamphodipropionate,
Disodium Stearoamphodiacetate,
Disodium Tallowamphodiacetate, and
Disodium Wheatgermamphodiacetate.

The anionic surfactants are more especially chosen from:
gemini surfactants such as for example disodium ethylene dicocamide PEG-15 disulfate (INCI name) sold for example under the trade name Ceralution H.
salts (especially alkali metal salts, especially sodium salts, ammonium salts, amino salts such as amino alcohol salts or alkaline-earth metal salts such as magnesium salts) of the following compounds:
alkyl sulfates, alkyl ether sulfates, alkylamido ether sulfates, alkylaryl polyether sulfates, monoglyceride sulfates;
alkyl sulfonates, alkyl amide sulfonates, alkyl aryl sulfonates, α-olefin sulfonates, paraffin sulfonates;
alkyl phosphates, alkyl ether phosphates;
alkyl sulfosuccinates, alkyl ether sulfosuccinates, alkyl amide sulfosuccinates; alkyl sulfosuccinamates;
alkyl sulfoacetates;
acyl sarcosinates; acylisethionates and N-acyl taurates;
salts of fatty acids such as oleic acid, ricinoleic acid, palmitic acid or stearic acid, coconut oil acid or hydrogenated coconut oil acid;
alkyl-D-galactoside uronic acid salts;
acyl lactylates;
salts of polyoxyalkylenated alkyl ether carboxylic acids, of polyoxyalkylenated alkylaryl ether carboxylic acids or of polyoxyalkylenated alkylamido ether carboxylic acids, in particular those containing from 2 to 50 ethylene oxide groups;
and mixtures thereof.

The alkyl or acyl substituent of these various compounds advantageously contains from 6 to 24 carbon atoms, and preferably from 8 to 24 carbon atoms, and the aryl substituent preferably denotes a phenyl or benzyl group.

Preferably a ($C_{12}$-$C_{20}$)alkyl phosphate and particularly a cetylphosphate will be used, for example potassium cetylphosphate, such as the one sold for example under the trade name Amphisol K.
glyceryl stearate (and) disodium ethylene dicocamide PEG-15 disulfate (and) glyceryl stearate citrate, a $C_{12}$-$C_{20}$ fatty acid salt such as triethanolamine stearate-glyceryl stearate (and) PEG-100 Stearate (INCI name), alone or in mixtures, sold for example under the trade name Arlacel 165,
stearic acid,
stearyl alcohol, and
any mixture thereof.

According to the invention, the surfactant with HLB greater than 7 is preferably a non-ionic surfactant.

The surfactants in accordance with the invention are chosen preferably from water-soluble silicones including at least one terminal or pendant, monovalent, polyoxyalkylated group.

The surfactants in accordance with the invention are chosen more preferentially from water-soluble silicones including at least one polyoxyalkylated group having the following general formula (a):

$$R_3SiO(R_2SiO)_p(RPESiO)_qSiR_3 \qquad (a)$$

in which:
the R substituents, the same or different, denote a monovalent hydrocarbon substituent chosen from alkyl, aryl and aralkyl substituents having at most 10 carbon atoms; some R substituents may also additionally contain an ethylcyclohexylene monoxide group having formula:

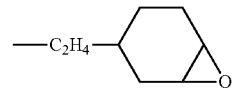

and are in low proportions in the polysiloxane chain;
p varies from 0 to 150, preferably from 0 to 100 and more preferentially from 0 to 30;
q varies from 1 to 12, preferably from 1 to 10 and more preferentially from 1 to 8; and
the PE polyether group has the following formula (b):

$$-C_xH_{2x}(OC_2H_4)_y(OC_3H_6)_zOR' \qquad (b)$$

in which:
x ranges from 1 to 8 and preferably ranges from 2 to 4 and more preferentially is 3;
y is greater than 0;
z is greater than or equal to 0;
the values from y and z are such that the total molecular weight of the polyoxyalkylenated portion of the PE polyether group varies from 200 to 10000 and more preferentially from 350 to 4000; and
R' denotes hydrogen, a $C_1$-$C_8$ alkyl group or a $C_2$-$C_8$ acyl group.

It should be noted that when z is other than 0, the polyoxyethylene and polyoxypropylene units may be distributed randomly along the PE polyether chain or distributed in blocks or both distributed in blocks and randomly.

Preferably, the R substituents are chosen from lower $C_1$-$C_6$ alkyls such as methyl, ethyl, butyl and hexyl, and from phenyl and benzyl. More particularly, the R substituents are chosen from $C_1$-$C_4$ lower alkyls and even more particularly denote methyl.

Preferably, the R' substituents are chosen from $C_1$-$C_4$ lower alkyls and even more particularly denote methyl.

The number of oxyethylene units in the PE group must be sufficient to produce a turbidity point in water between 25 and 90° C. and more preferentially from 40 to 70° C.

Water-soluble silicones having formula (a) may be obtained by the method described in U.S. Pat. No. 4,847,398.

Among water-soluble silicones having formula (a), use will preferably be made of that with the following formula (a'):

$$MeSiO(MeSiO)_p(MePESiO)_qSiMe_3 \qquad (a')$$

where Me denotes methyl and PE denotes:

$$-(CH_2)_3O(OC_2H_4)_y(OC_3H_6)_zOR' \qquad (b')$$

where x, y and z have the same values indicated above and R' denotes hydrogen or a $C_1$-$C_4$ alkyl group and more particularly methyl.

As another family of water-soluble silicones that can be used according to the invention, mention may be made of branched silicones having the following formula (c):

$$(MeSiO)_{q-2}[SiOMe_2]_{p/q}OPE]_q \qquad (c)$$

where p, q have the same values indicated above in formula (a); Me signifies methyl; and PE denotes the group having the following formula (d):

—(OC$_2$H$_4$)$_y$(OC$_3$H$_6$)$_z$R'     (d)

where y and z have the same values indicated above in formula (b) and R' denotes a C$_1$-C$_4$ alkyl group, and more particularly methyl.

Such silicones are for example sold by company OSI under the trade names Silwet L-720®, Silwet L-7002®, Silwet L-7600®, Silwet L-7604®, Silwet L-7605®, Silwet L-7607®, Silwet 1614, Silwet L-7657®, Silwet L-7200®, Silsoft L7230, Silsoft 305, Silsoft 820, Silsoft 880 or by the company Goldschmidt under the trade names Tego wet 260, Tegowet 500, Tegowet 505 and Tegowet 510®.

The silicone-containing surfactants are especially:
- bis-PEG/PPG-16/16 PEG/PPG-16/16 dimethicone (INCI name), sold for example under the trade name Abil Care 85 by Goldschmidt,
- PEG-12 dimethicone (INCI name), sold for example under the trade name Silsoft 880 by the company Momentive Performance Materials,
- PEG-11 methyl ether dimethicone, sold for example under the trade name KF 351 by the company Shin Etsu, and
- dimethicone copolyol benzoate (partial ester of benzoic acid and dimethicone copolyol, this being a dimethylpolysiloxane polymer including polyoxyethylene and/or polyoxypropylene side chains), sold for example under the name Finsolv SLB 101® and 201® by the company Fintex.

According to one embodiment, the surfactant with HLB greater than 7 is chosen from polysorbate 20, bis-PEG/PPG-16/16 PEG/PPG-16/16 dimethicone, PEG-12 dimethicone, and mixtures thereof.

According to a preferred embodiment, the composition according to the invention comprises PEG-12 dimethicone and/or bis-PEG-18 methyl ether dimethyl silane.

According to the invention, the surfactant or surfactants are present at concentrations ranging from 0.1% to 10% by weight, preferably from 0.25% to 5% by weight, and more particularly from 0.5% to 3% by weight relative to the total weight of the composition.

According to a preferred embodiment, the composition according to the invention comprises:
- from 0.1% to 50% by weight of photonic particles with respect to the total weight of said composition, said photonic particles having an average size comprised from 0.5 μm to 100 μm and each including an arrangement that diffracts monodisperse nanoparticles or voids, the diffraction spectrum of this arrangement including a reflection peak of the first order in the range of wavelengths ranging from 250 nm to 1800 nm, preferably from 250 nm to 400 nm,
- from 0.01% to 60% by weight of at least one absorber relative to the total weight of said composition, said absorber comprising at least one water-soluble organic UV filter, and
- from 0.1% to 10% by weight of a surfactant relative to the total weight of said composition, said surfactant being preferably a non-ionic surfactant with HLB greater than 7, preferentially a water-soluble silicone including at least one monovalent, terminal or pendant polyoxyalkylenated group.

Preferably, the mass ratio of the photonic particles on the surfactant is preferably from 0.5 to 100, preferably from 1 to 20.

The composition of the invention may include a phase that is liquid at 25° C. and contains the solid photonic particles.

The composition according to the invention may be aqueous; the photonic particles may be contained, preferably dispersed, in an aqueous phase.

"Aqueous composition" denotes a medium that is liquid at room temperature and atmospheric pressure that contains a high fraction of water relative to the total weight of the medium. The water mass content of the aqueous composition is preferably greater than or equal to 10%, advantageously to 30%, preferentially to 40%, or greater than 50%.

The composition may be single phase or have multiple phases.

The composition of the invention may alternatively be anhydrous and free of water.

The composition according to the invention may be oily; the photonic particles may be contained, preferably dispersed, in an oil phase.

The composition according to the invention may also contain at least one polar organic solvent, preferably a physiologically acceptable solvent.

The polar organic solvents are generally miscible with water.

As polar organic solvent, mention may be made of C$_1$-C$_6$ monoalcohols such as ethanol or isopropanol; C$_1$-C$_6$ polyols such as glycerine, 1,3-propanediol, 1,4-butanediol, 1,5-pentanediol and 1,6-hexanediol; C$_1$-C$_6$ alkylene glycols such as ethylene glycol, propylene glycol, dipropylene glycol, butylene glycol, pentylene glycol and hexylene glycol; and mixtures thereof.

The total C$_1$-C$_6$ alcohol content in the composition of the invention is preferably from 0.01% to 50% by weight, preferentially from 1% to 10% by weight of C$_1$-C$_6$ alcohols relative to the total weight of the composition.

The total C$_1$-C$_6$ alkylene glycol content in the composition of the invention is preferably from 0.1% to 30% by weight, preferentially from 5% to 25% by weight of C$_1$-C$_6$ alkylene glycols relative to the total weight of the composition.

The composition according to the invention may be transparent or translucent, and coloured or colourless. The composition according to the invention containing the photonic particles may contain no pigment or colourant. The colour may correspond to the addition of an additional colouring agent or of an absorber as defined above.

The composition according to the invention may include a volatile solvent.

"Volatile solvent" is understood in the sense of the invention to be any liquid that can evaporate on contact with keratin substances, at room temperature and atmospheric pressure.

The composition according to the invention may especially be chosen so that the composition contains at least 5%, even at least 30%, even at least 40% of volatile solvent.

The composition according to the invention may include a film-forming polymer that improves the persistence of the protection.

Film-Forming Polymer

In the present invention, the term "film-forming polymer" means a polymer that can, by itself or in the presence of an auxiliary film-forming agent, form a macroscopically continuous film that adheres to keratin substances, and preferably a cohesive film, and better still a film whose cohesion and mechanical properties are such that said film can be isolated and manipulated separately, for example when said film is made by casting onto a non-stick surface, for instance a Teflon-coated or silicone-coated surface.

The composition may include an aqueous phase, and the film-forming polymer may be present in this aqueous phase. In this case, it will preferably be a polymer in dispersion or an amphiphilic or associative polymer.

The term "polymer in dispersion" means water-insoluble polymers present in the form of particles of variable size. The polymer may or may not be crosslinked. The size of the polymer particles is typically between 25 and 500 nanometres and preferably between 50 and 200 nanometres. The following polymers in aqueous dispersion may be used: Ultrasol 2075® from Ganz Chemical, Daitosol 5000AD® from Daito Kasei, Avalure UR 450® from Noveon, DYNAMX® from National Starch, Syntran 5760® from Interpolymer, Acusol OP 301® from Rohm and Haas, Neocryl A 1090® from Avecia.

The acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Allianz OPT by the company Rohm and Haas, aqueous dispersions of acrylic or styrene/acrylic polymers sold under the brand name Joncryl® by the company Johnson Polymer, or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulfopolyesters sold under the brand name Eastman AQ® by the company Eastman Chemical Products, and vinyl dispersions, for instance Mexomer PAM® from the company Chimex, and mixtures thereof, are other examples of aqueous dispersions of water-dispersible film-forming polymer particles.

The term "amphiphilic or associative polymers" means polymers comprising one or more hydrophilic parts that make them partially water-soluble and one or more hydrophobic parts via which the polymers associate or interact. The following associative polymers may be used: Nuvis FX1100® from Elementis, Aculyn 22®, Aculyn 44®, Aculyn 46® from Rohm and Haas, Viscophobe DB1000® from Amerchol. Diblock copolymers formed from a hydrophilic block (polyacrylate or polyethylene glycol) and from a hydrophobic block (polystyrene or polysiloxane) may also be used.

The composition may comprise an oil phase and the film-forming polymer may be present in this oil phase. The polymer may then be in dispersion or in solution. NAD (non-aqueous dispersion) polymers or microgels (for example KSG) may be used, as may PS-PA polymers or styrene-based copolymers (Kraton, Regalite).

As examples of non-aqueous dispersions of polymer particles in one or more silicone and/or hydrocarbon-based oils, which may be surface-stabilized with at least one stabilizer, especially a block, grafted or random polymer, mention may be made of acrylic dispersions in isododecane, for instance Mexomer PAP® from the company Chimex, and dispersions of particles of a grafted ethylene polymer, preferably an acrylic polymer, in a liquid oil phase, the ethylene polymer advantageously being dispersed in the absence of additional stabilizer at the surface of the particles as described especially in document WO 04/055 081.

Among the film-forming polymers that may be used in the composition of the present invention, mention may be made of synthetic polymers, of free-radical type or of polycondensate type, polymers of natural origin, and mixtures thereof.

The film-forming polymers of free-radical type may be, especially, vinyl polymers or copolymers, especially acrylic polymers.

The vinyl film-forming polymers may result from the polymerization of monomers with ethylene unsaturation having at least one acid group and/or esters of these acid monomers and/or amides of these acid monomers such as unsaturated α,β-ethylene carboxylic acids such as acrylic acid, methacrylic acid, crotonic acid, maleic acid, itaconic acid.

The polymers of natural origin, optionally modified, may be chosen from shellac resin, sandarac gum, dammar resins, elemi gums, copals, cellulose polymers, such as nitrocellulose, ethylcellulose or nitrocellulose esters chosen for example from among cellulose acetate, cellulose acetobutyrate, cellulose acetopropionate, and mixtures thereof.

The film-forming polymer may be present in the form of solid particles in an aqueous or oil dispersion, which is generally known as a latex or pseudolatex. The film-forming polymer may include one or more stable dispersions of essentially spherical polymer particles of one or more polymers, in a physiologically acceptable oil phase. These dispersions are generally called NAD of polymers by contrast with latexes, which are aqueous polymer dispersions. These dispersions may especially be in the form of polymer nanoparticles in stable dispersion in said oil phase. The nanoparticles preferably have a mean size of between 5 and 600 nm. Techniques for preparing these dispersions are well known to those skilled in the art.

The composition may comprise at least one film-forming polymer that is a sequenced, linear, film-forming ethylene polymer. This polymer may comprise at least one first block and at least one second block that have different glass transition temperatures (Tg), said first and second blocks being linked together via an intermediate block comprising at least one constituent monomer of the first block and at least one constituent monomer of the second block. For example, the first and second blocks and of the block polymer are mutually incompatible. Such polymers are described, for example, in documents EP 1411069 or WO 04/028488, which are incorporated by reference.

Oil Phase

Although the composition containing the photonic particles could be oil-free, the composition according to the invention may nevertheless include in some embodiments an oil phase. The photonic particles may be contained in this oil phase or not.

The oil phase may especially be volatile.

The composition may include an oil such as for example synthetic esters and ethers, linear or branched hydrocarbons of mineral or synthetic origin, fatty alcohols having from 8 to 26 carbon atoms, partially hydrocarbon-based and/or silicone-based fluorinated oils, silicone oils such as volatile or non-volatile polymethylsiloxanes (PDMS) with linear or cyclic silicone chains, that are liquid or pasty at room temperature and mixtures thereof, other examples being given hereinafter.

A composition according to the invention may therefore comprise at least one volatile oil.

Volatile Oils

For the purposes of the present invention, "volatile oil" means an oil (or non-aqueous medium) that is capable of evaporating on contact with the skin in less than one hour, at room temperature and at atmospheric pressure.

The volatile oil is a volatile cosmetic oil, which is liquid at room temperature, especially having a non-zero vapour pressure, at room temperature and atmospheric pressure, especially having a vapour pressure ranging from 0.13 Pa to 40 000 Pa ($10^{-3}$ to 300 mmHg), preferably ranging from 1.3 Pa to 13 000 Pa (0.01 to 100 mmHg) and preferably ranging from 1.3 Pa to 1300 Pa (0.01 to 10 mmHg).

The volatile hydrocarbon-based oils may be chosen from hydrocarbon-based oils containing from 8 to 16 carbon atoms, and especially branched $C_8$-$C_{16}$ alkanes (also known as isoparaffins), for instance isododecane (also known as 2,2,4,4,6-pentamethylheptane), isodecane, isohexadecane and, for example, the oils sold under the trade names Isopar® or Permethyl®.

Volatile oils that may also be used include volatile silicones, for instance volatile linear or cyclic silicone oils, especially those with a viscosity centistokes ($8\times10^{-6}$ $m^2$/s), and especially containing from 2 to 10 silicon atoms and especially from 2 to 7 silicon atoms, these silicones optionally comprising alkyl or alkoxy groups containing from 1 to 10 carbon atoms. As volatile silicone oils that may be used in the invention, mention may be made especially of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethyl-cyclopentane, and mixtures thereof, may also be used.

It is also possible to use a mixture of the oils mentioned above.

Non-Volatile Oils

A composition according to the invention may include a non-volatile oil.

For the purposes of the present invention, "non-volatile oil" means an oil with a vapour pressure of less than 0.13 Pa and especially oils with high molar mass.

The non-volatile oils may be chosen especially from non-volatile hydrocarbon-based oils, which may be fluorinated, and/or non-volatile silicone oils.

As non-volatile hydrocarbon-based oils that are suitable for use in the invention, mention may be made especially of:
  hydrocarbon-based oils of animal origin,
  hydrocarbon-based oils of plant origin such as phytostearyl esters, such as phytostearyl oleate, phytostearyl isostearate and lauroyl/octyl-dodecyl/phytostearyl glutamate, for example sold under the name Eldew PS203 by Ajinomoto, triglycerides consisting of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or alternatively caprylic/capric acid triglycerides, for instance those sold by the company Stearineries Dubois or those sold under the names Miglyol 810®, 812® and 818® by the company Dynamit Nobel,
  hydrocarbon-based oils of mineral or synthetic origin, for instance:
    synthetic ethers containing from 10 to 40 carbon atoms;
    linear or branched hydrocarbons of mineral or synthetic origin, such as petroleum jelly, polydecenes, hydrogenated polyisobutene such as Parleam, and squalane, and mixtures thereof, and in particular hydrogenated polyisobutene,
    synthetic esters, for instance oils having formula $R_1COOR_2$ in which $R_1$ represents a linear or branched fatty acid residue containing from 1 to 40 carbon atoms and $R_2$ represents a hydrocarbon-based chain that is especially branched, containing from 1 to 40 carbon atoms provided that $R_1+R_2\geq10$.

The esters may be especially chosen from esters, especially fatty acid esters such as for example:
  cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoate, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;
  polyol esters and pentaerythritol esters, for instance dipentaerythrityl tetrahydroxystearate/tetraisostearate,
  esters of diol dimers and of diacid dimers, such as Lusplan DD-DA5® and Lusplan DD-DA7® sold by the company Nippon Fine Chemical and described in patent application FR 03/02809,
  fatty alcohols that are liquid at room temperature, with a branched and/or unsaturated carbon chain containing from 12 to 26 carbon atoms, for instance 2-octyldodecanol, isostearyl alcohol, oleyl alcohol, 2-hexyldecanol, 2-butyloctanol and 2-undecylpentadecanol,
  higher fatty acids such as oleic acid, linoleic acid and linolenic acid, and mixtures thereof, and
  dialkyl carbonates, where the two alkyl chains can be the same or different, such as dicaprylyl carbonate sold under the name Cetiol CC® by Cognis,
  non-volatile silicone oils, for instance non-volatile polydimethylsiloxanes (PDMSs), polydimethylsiloxanes comprising alkyl or alkoxy groups that are pendant and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof,
and mixtures thereof.

Complementary and Additional Filters

The composition including the photonic particles may include at least one additive chosen from the adjuvants typical of the cosmetic domain, such as fillers, colourants, hydrophilic or lipophilic gellants, water-soluble or liposoluble actives, preservatives, moisturizers such as polyols and especially glycerine, sequestrants, antioxidants, solvents, fragrances, physical and chemical sunscreens, especially those that filter UVA and/or UVB, odour absorbers, pH adjusters (acids or bases) and mixtures thereof.

As fillers which can be used in the composition according to the invention, mention may be made, for example, of pigments; silica powder; polyamide particles and in particular those sold under the name ORGASOL by the company Atochem; polyethylene powders; powders of natural organic materials such as starch powders, especially of corn starch, wheat or rice, crosslinked or otherwise, such as the powders of starch crosslinked with octenyl succinate anhydride, sold under the name DRY-FLO by the company National Starch; microspheres based on acrylic copolymers, such as copolymer of ethylene glycol dimethacrylate/lauryl methacrylate copolymer sold by Dow Corning under the name POLYTRAP; powders of polymethylmethacrylate such as those marketed under the name MICROPEARL M 100 by the company Matsumoto; expanded powders such as hollow microspheres and especially the microspheres sold under the name EXPANCEL by Kemanord Plast or under the name MICROPEARL F 80 ED by Matsumoto; silicone resin microbeads such as those sold under the name TOSPEARL by the company Toshiba Silicone; polyurethane powders such as the powder copolymer hexamethylene diisocyanate/trimethylol hexyllactone sold under the name Plastic Powder D-400 by Toshiba Pigment Company (CTFA name: HDI/trimethylol hexyllactone Crosspolymer); and mixtures thereof. When present, these fillers can be in amounts ranging from 0.001% to 30% by weight, preferably from 0.1% to 20% by weight and better still from 1% to 10% by weight relative to the total weight of the composition.

The composition may also contain at least one active having complementary activity in the domain of sun protection, such as antioxidants, whitening agents in the scope of anti-pigmentation and depigmentation, anti-ageing actives.

Additional filters that are organic, hydrophobic or insoluble in the usual solvents, may especially be chosen from different families of chemical compounds.

Hydrophobic Filters that can Absorb UV from 320 to 400 nm (UVA)

Dibenzoylmethane Derivatives:

Butyl methoxydibenzoylmethane sold especially under the trade name Parsol 1789 by DSM Nutritional Products, Inc., Isopropyldibenzoylmethane.

Aminobenzophenones n-Hexyl 2-(4-diethylamino-2-hydroxybenzoyl)-benzoate sold under the trade name Uvinul A+ by BASF.

Anthranilic Derivatives

Menthyl anthranilate sold under the trade name Neo Heliopan MA by Symrise.

4,4-Diarylbutadiene Derivatives 1,1-Dicarboxy(2,2'-dimethylpropyl)-4,4-diphenylbutadiene, The preferred filters are butyl methoxydibenzoylmethane and n-hexyl 2-(4-diethylamino-2-hydroxybenzoyl)-benzoate.

Hydrophobic Filters that can Absorb UV from 280 to 320 nm (UVB)

Para-Aminobenzoates

Ethyl PABA,

Ethyl dihydroxypropyl PABA,

Ethylhexyl Dimethyl PABA (Escalol 507 from ISP),

Salicylic Derivatives

Homosalate sold under the name Eusolex HMS by Rona/EM Industries,

Ethylhexyl salicylate, sold under the name Neo Heliopan OS by Symrise,

Dipropylene glycol salicylate sold under the name Dipsal by Scher,

TEA salicylate, sold under the name Neo Heliopan TS® by Symrise.

Cinnamates

Ethylhexyl methoxycinnamate sold in particular under the trade name Parsol MCX by DSM Nutritional Products, Inc., Isopropyl methoxycinnamate, Isoamyl methoxycinnamate sold under the trade name Neo Heliopan E 1000 by Symrise, Diisopropyl methyl cinnamate, Cinoxate, Glyceryl ethylhexanoate dimethoxycinnamate.

β,β'-Diphenylacrylate Derivatives

Octocrylene sold especially under the trade name Uvinul N539 by BASF,

Etocrylene sold especially under the trade name Uvinul N35 by BASF.

Benzylidene Camphor Derivatives

3-Benzylidene camphor manufactured under the name Mexoryl SD by Chimex,

Methylbenzylidene camphor sold under the name Eusolex 6300 by Merck,

Polyacrylamidomethylbenzylidene camphor manufactured under the name Mexoryl SW by Chimex.

Triazine Derivatives ethylhexyltriazone sold especially under the trade name Uvinul T150 by BASF, Diethylhexyl butamido triazone, sold under the trade name Uvasorb HEB by Sigma 3V, 2,4,6-tris-(dineopentyl-4'-aminobenzalmalonate)-s-triazine, 2,4,6-tris-(diisobutyl-4'-amino benzalmalonate)-s-triazine, 2,4-bis-(dineopentyl-4'-aminobenzalmalonate)-6-(n-butyl-4'-aminobenzoate)-s-triazine, 2,4-bis(n-butyl 4'-aminobenzoate)-6-(aminopropyltrisiloxane)-s-triazine, the symmetrical triazine filters described in U.S. Pat. No. 6,225,467, patent application WO 2004/085 412 (see compounds 6 and 9) or the document "Symmetrical Triazine Derivatives" IP.COM Journal, IP.COM Inc West Henrietta, N.Y., USA (Sep. 20, 2004) in particular 2,4,6-tris-(diphenyl)-1,3,5-triazines (in particular 2,4,6-tris(diphenyl-4-yl-1,3,5-triazine) and 2,4,6-tris(terphenyl)-1,3,5-triazine, which is described in the Beiersdorf applications WO 06/035000, WO 06/034982, WO 06/034991, WO 06/035007, WO 2006/034992, WO 2006/034985.

Imidazoline Derivatives

Ethylhexyl dimethoxybenzylidene dioxoimidazo line propionate.

Benzalmalonate Derivatives

Polyorganosiloxanes containing benzalmalonate functions such as Polysilicone-15, sold under the trade name Parsol SLX by DSM Nutritional Products, Inc., Di-neopentyl-4'-methoxybenzalmalonate.

Merocyanine Derivatives

Octyl-5-N,N-diethylamino-2-phenylsulfonyl-2,4-pentadienoate.

The preferred filters are homosalate, ethylhexylsalicylate, octocrylene, ethylhexyl, methoxycinnamate v, isoamyl methoxycinnamate, ethylhexyl triazone, diethylhexyl butamido triazone.

The most preferred are ethylhexylsalicylate, octocrylene, ethylhexyl triazone, ethylhexyl methoxycinnamate.

Mixed Hydrophobic Filters that can Absorb Both UVA and UVB

Benzophenone Derivatives

Benzophenone-1 sold under the trade name Uvinul 400 by BASF,

Benzophenone-2 sold under the trade name Uvinul D50 by BASF,

Benzophenone-3 or oxybenzone sold under the trade name Uvinul M40 by BASF,

Benzophenone-5,

Benzophenone-6 sold under the trade name Helisorb 11 by Norquay,

Benzophenone-8 sold under the trade name Spectra-Sorb UV-24 by American Cyanamid, Benzophenone-10, Benzophenone-11, Benzophenone-12, Phenylbenzotriazole Derivatives Drometrizole trisiloxane sold under the name Silatrizole by Rhodia Chimie, methylenebis(benzotriazolyl)tetramethylbutylphenol sold in solid form under the trade name MIXXIM BB/100 by Fairmount Chemical, or in micronized form as an aqueous dispersion under the trade name Tinosorb M by Ciba Specialty Chemicals, Bis-Resorcinyl Triazine Derivatives Bis(ethylhexyloxyphenol)methoxyphenyltriazine sold under the trade name Tinosorb S by Ciba Geigy, Benzoxazole Derivatives 2,4-bis[5-(1-Dimethylpropyl)benzoxazol-2-yl(4-phenyl)imino]-6-(2-ethylhexyl)imino-1,3,5-triazine sold under the name Uvasorb K2A by Sigma 3V, The preferred filters are:

Drometrizole trisiloxane,

Methylene bis-benzotriazolyl tetramethylbutylphenol,

Bis(ethylhexyloxyphenol) methoxyphenyltriazine, and

3-Benzophenone or oxybenzone,

The most preferred filters are:

Drometrizole trisiloxane, and

Bis(ethylhexyloxyphenol)methoxyphenyltriazine.

Mention may also be made of merocyanine filters having the following formula, and its E/E- and E/Z-geometric isomers:

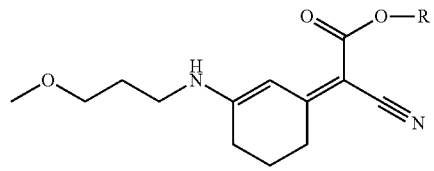

in which:

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, where said groups can be interspersed by one or more O.

The merocyanine filters may in their E/E-, E/Z-geometric isomer forms.

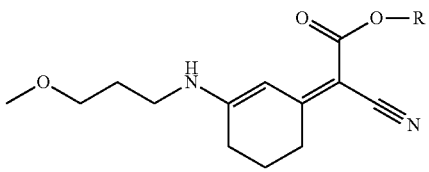

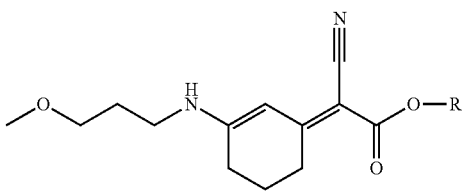

The preferred merocyanine filters are those where R is a $C_1$-$C_{22}$ alkyl that can be interspersed by one or more O.

Among merocyanine filters, most particularly those chosen from the following compounds will be used, and their E/E-, E/Z-geometric isomers:

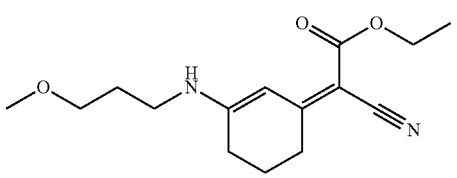

ethyl (2Z)-cyano {3-[(3-methoxypropyl)amino]cyclohex-2-en-1-ylidene} ethanoate

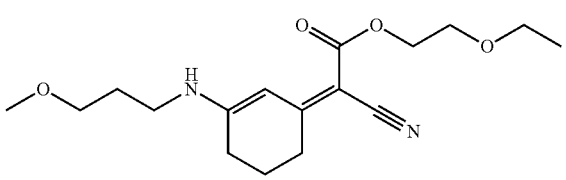 [SMILES: CCOCCOC(=O)/C(C#N)=C1\C=C(NCCCOC)CCC1]

2-ethoxyethyl (2Z)-cyano {3-[(3-methoxypropyl)amino]cyclohex-2-en-1-ylidene} ethanoate

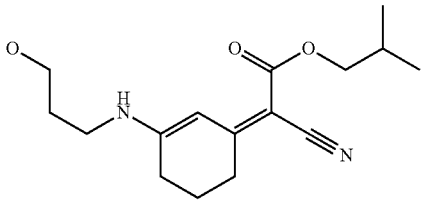

2-methylpropyl (2Z)-cyano {3-[(3-methoxypropyl)amino]cyclohex-2-en-1-ylidene} ethanoate -continued

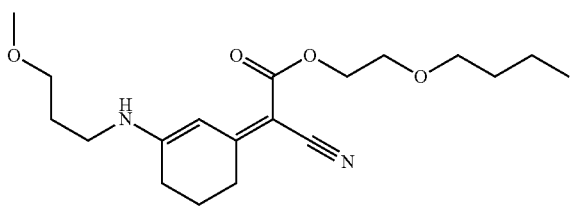

2-butoxyethyl (2Z)-cyano {3-[(3-methoxypropyl)amino]cyclohex-2-en-1-ylidene} ethanoate

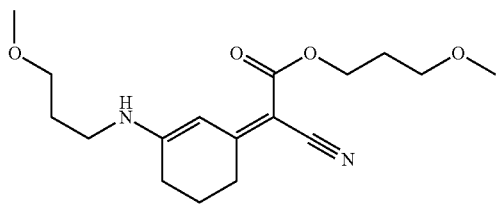

3-methoxypropyl (2Z)-cyano {3-[(3-methoxypropyl)amino]cyclohex-2-en-1-ylidene} ethanoate

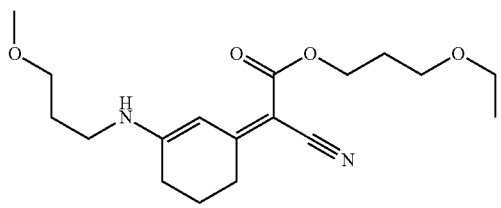

3-ethoxypropyl (2Z)-cyano {3-[(3-methoxypropyl)amino]cyclohex-2-en-1-ylidene} ethanoate According to a more particularly preferred embodiment of the invention, the compound 2-ethoxyethyl (2Z)-cyano {3-[(3-methoxypropyl)-amino]cyclohex-2-en-1-ylidene}ethanoate (2) is used in its E/Z geometric configuration with the following structure:

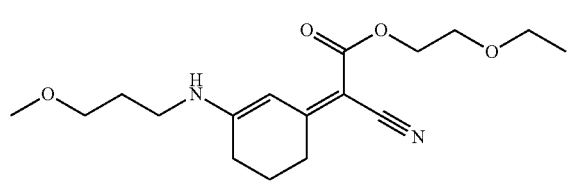

and/or in its E/E geometric configuration with the following structure:

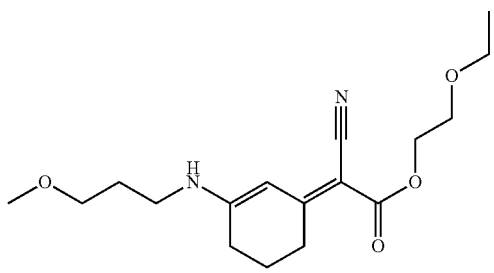 [SMILES: CCOCCOC(=O)/C(C#N)=C1/C=C(NCCCOC)CCC1]

The merocyanine filters above may be prepared according the protocols described in WO 2007/071582, in IP.com Journal (2009), 9(5A), 29-30 IPCOM000182396D under the title "Process for producing 3-amino-2-cyclohexan-1-ylidene compounds" and in U.S. Pat. No. 4,749,643 (col.13, 1.66-col.14, 1.57 and the references cited in that regard).

Inorganic Sunscreens or Photoprotectors

The inorganic photoprotective agents are chosen from coated or uncoated metal oxide pigments (mean size of the primary particles: generally between 5 nm and 100 nm, preferably between 10 nm and 50 nm), for instance titanium oxide (amorphous or crystallized in rutile and/or anatase form), iron oxide, zinc oxide, zirconium oxide or cerium oxide pigments, which are all UV-photoprotective agents that are well known per se.

The pigments may be coated or uncoated.

The coated pigments are pigments that have undergone one or more surface treatments of chemical, electronic, mechanochemical and/or mechanical nature with compounds such as described for example in Cosmetics & Toiletries, February 1990, Vol. 105, p. 53-64, such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and consist essentially of a repetition of main units in which the silicon atoms are linked together via oxygen atoms (siloxane bond), optionally substituted hydrocarbon-based substituents being directly attached via a carbon atom to said silicon atoms.

The term "silicones" also encompasses the silanes necessary for their preparation, in particular alkylsilanes.

The silicones used for coating the nanopigments that are suitable for the present invention are preferably chosen from the group containing alkylsilanes, polydialkylsiloxanes and polyalkylhydrogensiloxanes. Even more preferentially, the silicones are chosen from the group containing octyltrimethylsilane, polydimethylsiloxanes and polymethylhydrogensiloxanes.

Of course, the pigments formed of metal oxides may, before their treatment with silicones, have been treated with other surfacing agents, in particular with cerium oxide, alumina, silica, aluminium compounds, silicon compounds or mixtures thereof.

The coated pigments are more particularly titanium oxides that have been coated:
- with silica, such as the product Sunveil from Ikeda,
- with silica and iron oxide, such as the product Sunveil F from Ikeda,
- with silica and alumina, such as the products Microtitanium Dioxide MT 500 SA and Microtitanium Dioxide MT 100 SA from the company Tayca and Tioveil from the company Tioxide,
- with alumina, such as the products Tipaque TTO-55 (B) and Tipaque TTO-55 (A) from Ishihara and UVT 14/4 from Kemira,
- with alumina and aluminium stearate, such as the products Microtitanium Dioxide MT 100 T, MT 100 TX, MT 100 Z and MT-01 from Tayca, the products Solaveil CT-10 W and Solaveil CT 100 from Uniqema and the product Eusolex T-AVO from Merck,
- with silica, alumina and alginic acid, such as the product MT-100 AQ from Tayca, with alumina and aluminium laurate, such as the product Microtitanium Dioxide MT 100 S from Tayca, with iron oxide and iron stearate, such as the product Microtitanium Dioxide MT 100 F from the company Tayca, with zinc oxide and zinc stearate, such as the product BR 351 from Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminium stearate and treated with a silicone, such as the product STT-30-DS from the company Titan Kogyo, with silica and treated with a silicone, such as the product UV-Titan X 195 from Kemira, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

$TiO_2$ treated with octyltrimethylsilane, sold under the trade name T 805 by the company Degussa Silices, $TiO_2$ treated with a polydimethylsiloxane, sold under the trade name 70250 Cardre UF TiO2SI3 by the company Cardre, anatase/rutile $TiO_2$ treated with a polydimethylhydrogensiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wackher under the name Transparent titanium oxide PW, by the company Miyoshi Kasei under the name UFTR, by the company Tomen under the name ITS and by the company Tioxide under the name Tioveil AQ.

The uncoated zinc oxide pigments are for example:
those sold under the Z-Cote name by Sunsmart,
those sold under the Nanox name by Elementis,
those sold under the name Nanogard WCD 2025 by Nanophase Technologies.

The coated zinc oxide pigments are for example:
those sold under the name Zinc Oxide CS-5 by Toshibi (ZnO coated with polymethylhydrosiloxane),
those sold under the name Nanogard Zinc Oxide FN by the company Nanophase Technologies (as a 40% dispersion in Finsolv TN, $C_{12}$-$C_{15}$ alkyl benzoate),
those sold under the name Daitopersion ZN-30 and Daitopersion ZN-50 by the company Daito (dispersions in cyclopolymethylsiloxane/oxyethylenated polydimethylsiloxane, containing 30% or 50% of nano zinc oxides coated with silica and polymethylhydrogensiloxane),
those sold under the name NFD Ultrafine ZnO by Daikin (ZnO coated with perfluoroalkyl phosphate and copolymer based on perfluoroalkylethyl as a dispersion in cyclopentasiloxane),
those sold under the name SPD-Z1 by Shin-Etsu (ZnO coated with silicone-grafted acrylic polymer, dispersed in cyclodimethylsiloxane),
those sold under the name Escalol Z100 by ISP (alumina-treated ZnO dispersed in an ethylhexyl methoxycinnamate/PVP-hexadecene copolymer/methicone mixture);
those sold under the name Fuji ZnO-SMS-10 by Fuji Pigment (ZnO coated with silica and polymethylsilsesquioxane);
those sold under the name Nanox Gel TN by the company Elementis (ZnO dispersed at a concentration of 55% in $C_{12}$-$C_{15}$ alkyl benzoate with hydroxystearic acid polycondensate).

The uncoated cerium oxide pigments are sold, for example, under the name Colloidal Cerium Oxide by the company Rhone-Poulenc.

The uncoated iron oxide pigments are sold, for example, by Arnaud under the names Nanogard WCD 2002 (FE 45B), Nanogard Iron FE 45 BL AQ, Nanogard FE 45R AQ and Nanogard WCD 2006 (FE 45R) or by Mitsubishi under the name TY-220.

The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, especially of titanium dioxide and of cerium dioxide, including the equal-weight mixture of titanium dioxide and cerium dioxide coated with silica, sold by the company Ikeda under the name Sunveil A, and also the mixture of titanium dioxide and zinc dioxide coated with alumina, silica and silicone, such as the product M 261 sold by the company Kemira, or coated with alumina, silica and glycerol, such as the product M 211 sold by the company Kemira.

The inorganic filters may be present in the compositions according to the invention in a concentration of between 0.1% and 15% and preferably between 0.2% and 10% by weight relative to the total weight of the composition.

The additive or additives may be chosen from those cited in the CTFA Cosmetic Ingredient Handbook, 10'h Edition Cosmetic and Fragrance Assn, Inc., Washington D.C. (2004), incorporated here by reference.

Clay

The composition according to the invention may further comprise at least one clay.

The presence of a clay in a composition comprising photonic particles, preferably in dispersion, permits to obtain a reversible sedimentation or a sedimentation without aggregation (or clogging) of the said particles, thus allowing, by simple agitation of the composition, to redisperse the photonic particles. From a sensory point of view, the photonic particles also permits to reduce the sticky feel due to the water-soluble UV screening agents. The addition of clay, in particular montmorillonite, also permits to compensate for the sticky side of the composition bound to the photonic particles.

The clays are products already well known per se, which are described, for example, in the book "Mineralogy of Clays, S. Caillere, S. Henin, M. Rautureau, 2nd Edition 1982, Masson" included for reference purposes.

Among the clays that may be mentioned by way of example are clays of the smectite family such as laponite and montmorillonite, from the family of kaolinites such as kaolinite, dickite, nacrite, optionally modified clays of the family halbysite, dombassite, antigorite, benthiérine, pyrophyllite, montmorillonites, beidellite, vermiculites, talc, stevensite, hectorites, bentonites, saponites, chlorites, Sepiolite and illite.

Formulation Forms

The composition according to the invention may be a lotion, a two-phase product (i.e. liquid/solid) or tri-phase product (solid/two non-miscible liquids), a cream, a milk, an ointment, a gel, for the skin, lips, hair or nails.

Photoprotective Cosmetic Composition

According to another of its features, the invention relates to a photoprotective cosmetic composition comprising, in a physiologically acceptable medium, a composition according to the invention as defined above.

"Physiologically acceptable medium" means a non-toxic medium that may be applied to human keratin substances, in particular the skin, mucous membranes and appendages.

The medium is suited to the nature of the support onto which the composition is to be applied, and also to the form in which the composition is intended to be packaged.

The composition may be packaged in any packaging device, especially made of a thermoplastic substance, or of any support intended for this purpose.

The packaging device may be a bottle, a pump bottle, an aerosol bottle, a tube, a bag, a jar.

In particular, and as shown in the following examples, the compositions in accordance with the invention are convenient for an application with most mechanical pumps. Indeed, the photonic particles are not blocking the orifices. The compositions can therefore be delivered in the form of a spray or light mist.

Non-Therapeutic Cosmetic Photoprotection Method

The photoprotective cosmetic composition may be applied by hand or using an applicator.

The application may also be via spray or projection using for example a piezoelectric device, an aerograph or by transferring a layer of the composition previously deposited on an intermediate support.

EXAMPLES

Example 1—Preparation of Photonic Particles in Accordance with the Invention

The aqueous dispersion of silica particles (COSMO S-160NP by JGC) was atomized according to the method described in the description.

The commercial dispersion is used as is, or mixed with water to obtain a mass concentration of particles equal to 18%.

The dispersion thereby obtained was added to an atomiser (NIRO MINOR PRODUCTION), with the injection flow rate set at 3800 g/h, the turbine speed set at 37800 rpm and the atomization temperature set at 290° C.

Example 2—Evaluation in Simplex Medium

The combination of the photonic particles obtained in Example 1 with an absorber and a wetting agent was first evaluated in a simplex formula.

| Ingredient | Mass % (active ingredient) | | |
| --- | --- | --- | --- |
| | Control a | Control b | Formula A |
| Photonic particles | — | 10.85 | 10.85 |
| Mexoryl SX (terephthalylidene dicamphor sulfonic acid) | 0.11 | — | 0.11 |

-continued

| Ingredient | Mass % (active ingredient) | | |
| --- | --- | --- | --- |
| | Control a | Control b | Formula A |
| Polysorbate 20 | 0.16 | 0.16 | 0.16 |
| Hydroxypropyl cellulose HPC (Klucel MF by Ashland) | 0.14 | 0.14 | 0.14 |
| Ethanol | 30.41 | 30.41 | 30.41 |
| Water | qs | qs | qs |
| Triethanolamine | 0.05 | — | 0.05 |

The experimental protocol is as follows:

added photonic particles from example 1 to a solution of absorber (Mexoryl SX) and surfactant (Polysorbate 20), weighed the water (qs), stirred with a magnetic stirring bar at room temperature for 3 hours, added amounts of HPC and ethanol solutions, stirred with the magnetic stirring bar and/or a vortex and/or sonication until homogenization, deposited the formula on a rimmed PMMA plate, dried for at least 2 hours, and measured absorbance on 3 different areas of the deposit.

The spectrophotometer used is a Cary 5000 UV-IR from brand Agilent Technologies.

By comparing the absorbance curves between the two controls a and b and formula A, an amplification (×18) of the efficacy of the absorber in the presence of photonic particles was observed.

Example 3—Preparation of Compositions in Accordance with the Invention

The evaluated combination of the photonic particles obtained in Example 1 with an absorber and a wetting agent was next confirmed in liquid two-phase (solid/liquid) aqueous formulations.

The following compositions are were prepared:

Control: photonic particles without absorber

Control No. 1: an absorber without photonic particles

Composition No. 1: an absorber with photonic particles

Control No. 2: an absorber without photonic particles

Composition No. 2: an absorber with photonic particles

Control No. 3: two absorbers without photonic particles

Composition No. 3: two absorbers with photonic particles.

Composition No. 4: an absorber with photonic particles

Composition No. 5: an absorber with photonic particles

Composition No. 6: two absorbers with photonic particles

|   |   | Control | Control No. 1 | Composition No. 1 | Control No. 2 | Composition No. 2 | Control No. 3 | Composition No. 3 | Composition no 4 |
|---|---|---|---|---|---|---|---|---|---|
| A | WATER | 61.52 | 52.76 | 45.18 | 41.60 | 33.52 | 25.26 | 17.68 | QS 100 |
|   | CAPRYLYL GLYCOL | 0.1 | 0.1 | 0.1 | 0.1 | 0.1 | 0.1 | 0.1 | 0.1 |
|   | PENTASODIUM ETHYLENEDIAMINE TETRAMETHYLENE PHOSPHONATE | 0.3 | 0.3 | 0.3 | 0.3 | 0.3 | 0.3 | 0.3 | 0.3 |
|   | PHENOXYETHANOL | 0.5 | 0.5 | 0.5 | 0.5 | 0.5 | 0.5 | 0.5 | 0.5 |
|   | COLOURANT | 0.0001 | 0.0001 | 0.0001 | 0.0001 | 0.0001 | 0.0001 | 0.0001 | 0.0001 |
|   | GLYCEROL | 3 | 3 | 3 | 3 | 3 | 3 | 3 | 3 |
|   | PROPYLENE GLYCOL | 6 | 6 | 6 | 6 | 6 | 6 | 6 | 6 |
|   | DIPROPYLENE GLYCOL | 10 | 10 | 10 | 10 | 10 | 10 | 10 | 10 |
|   | BUTYLENE GLYCOL | 4 | 4 | 4 | 4 | 4 | 4 | 4 | 4 |
|   | HEXYLENE GLYCOL | 1 | 1 | 1 | 1 | 1 | 1 | 1 | 1 |
|   | BIS-PEG-18 METHYL ETHER DIMETHYL SILANE | 1 | 1 | 1 | 1 | 1 | 1 | 1 | 1 |
|   | PEG-12 DIMETHICONE | 1 | 1 | 1 | 1 | 1 | 1 | 1 | 1 |
|   | DISODIUM RUTINYL DISULFATE (RONACARE RUTINSULFATE 130156 de MERCK) | 0 | 0 | 0 | 0 | 0 | 0 | 0 | 4 |
| B | Eusolex 232 PHENYLBENZIMIDAZOLE SULFONIC ACID | 0 | 4 | 4 | 0 | 0 | 4 | 4 | 0 |
|   | WATER | 0 | 10 | 10 | 0 | 0 | 10 | 10 | 0 |
|   | TROMETHAMINE | 0 | 2.34 | 2.34 | 0 | 0 | 2.34 | 2.34 | 2.34 |
| C | Mexoryl SX TEREPHTHALYLIDENE DICAMPHOR SULFONIC ACID | 0 | 0 | 0 | 15 | 15 | 15 | 15 | 0 |
|   | WATER | 0 | 0 | 0 | 10 | 10 | 10 | 10 | 10 |
|   | TRIETHANOLAMINE | 0 | 0 | 0 | 2.5 | 3 | 2.5 | 2.5 | 0 |
| D | Photonic particles according to Example 1 | 7.58 | 0 | 7.58 | 0 | 7.58 | 0 | 7.58 | 7.58 |
| E | ALCOHOL | 4 | 4 | 4 | 4 | 4 | 4 | 4 | 4 |
|   |   | 100.00 | 100.00 | 100.00 | 100.00 | 100.00 | 100.00 | 100.00 | 100.0 |

Preparation Method prepare phase C: weigh the phase and homogenize using a magnetic stirring bar, leave the mixture at room temperature for from 3 to 12 hours with mechanical stirring, prepare phase A and homogenize with a Rayneri, prepare phase B and stir with a magnetic stirring bar while heating to 50° C. until the Eusolex 232 has dissolved completely, add phase B to phase A, then add phase C at room temperature, add phase D, then phase E and homogenize for 10 minutes with a Rayneri.

Example 4—Other Compositions According to the Invention

|   | Composition N°5 | Composition N°6 |
|---|---|---|
| MT100-AQ (available from Tayca) TITANIUM DIOXIDE (and) SILICA (et) ALUMINUM HYDROXIDE (et) ALGINIC ACID | 10 | 5 |
| Particules photoniques selon l'exemple 1 | 7.58 | 7.58 |
| XANTHAN GUM | 2 | 2 |
| WATER | QSP 100 | QSP 100 |
| PHENYLBENZIMIDAZOLE SULFONIC ACID | 0 | 3.5 |
| TRIETHANOLAMINE | 0 | 2 |
| PROPYLENE GLYCOL | 3 | 3.5 |
| DIPROPYLENE GLYCOL | 3 | 2 |
| GLYCERIN | 8 | 8 |
| ETHANOL ABSOLU DENATURE | 3 | 3 |

These compositions were carried out according to the procedure related to that described in Example 3.

Example 5—In Vitro SPF Evaluation

Using a micropipette 30 mg of composition are deposited onto a PMMA plate 5 cm by 5 cm; the composition is spread with a finger, left to dry for 20 minutes, then the vitro SPF is measured using the Labsphère 2000.

|  | Control | Control No. 1 | Composition No. 1 | Control No. 2 | Composition No. 2 | Control No. 3 | Composition No. 3 |
|---|---|---|---|---|---|---|---|
| SPF In vitro | 1.25 | 8.34 | 10.88 | 6.70 | 9.33 | 21.03 | 45.54 |
| Standard deviation | ±0.14 | ±0.42 | ±0.79 | ±0.24 | ±1.08 | ±2.76 | ±8.11 |

Figure 2:
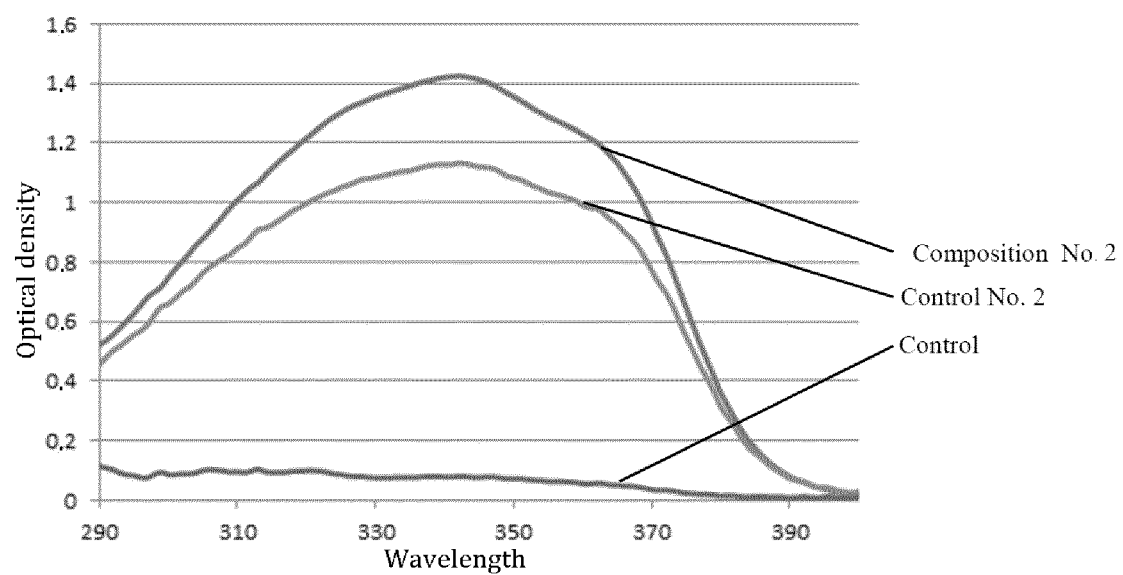
FIG. 2 represents an optical density curve for composition no. 2 and control composition no. 2 from the examples.
Figure 3:
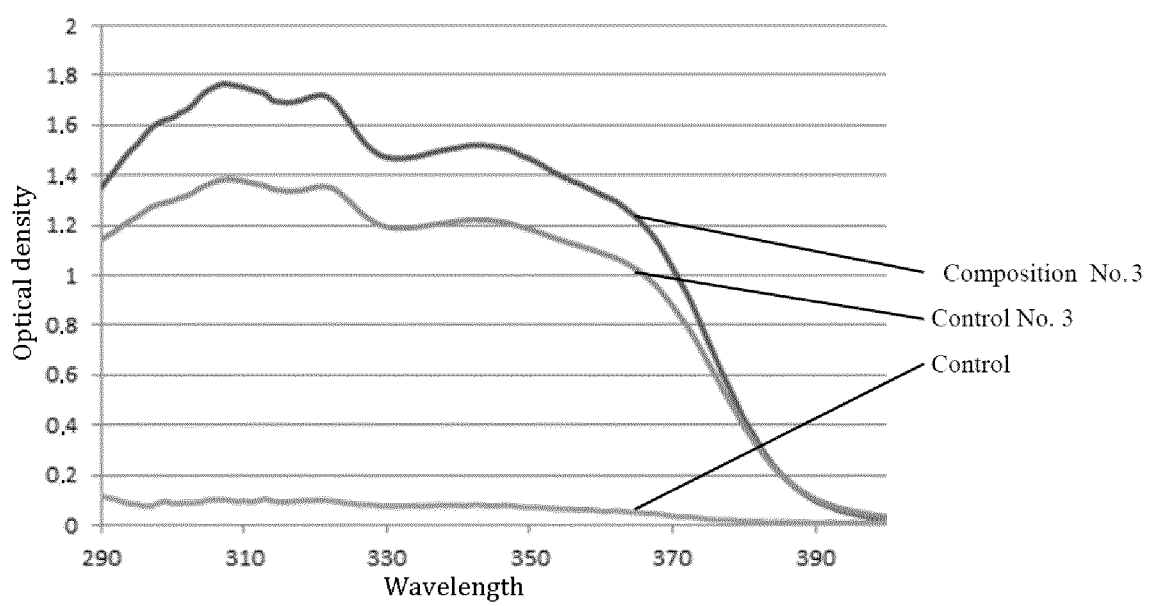
FIG. 3 represents an optical density curve for composition no. 3 and control composition no. 3 from the examples.

The optical density curves for the formulas prepared are shown in FIGS. 1 to 3.

An improvement in optical density of about 0.2 to 0.3 OD for the curves corresponding to the compositions in accordance with the invention (No. 1, No. 2 and No. 3) relative to the compositions devoid of photonic particles (controls No. 1, No. 2 and No. 3).

Example 6—In Vivo SPF Evaluation

Composition No. 3 in accordance with the invention was tested in vivo according to ISO method 24444 (2010), in comparison with the control composition No. 3 devoid of photonic particles.

|  | Control No. 3 | Formula No. 3 |
|---|---|---|
| in vivo SPF | 14.2 | 36.0 |
| Standard deviation | ±0.6 | ±2.7 |

From a sensorial point of view, the photonic particles also reduce the sticky feel due to the water-soluble UV filter.

What is more, their fast sedimentation rate produces a very clean phase separation between the liquid phase and the aqueous phase, thereby retaining the transparent liquid phase.

Finally, compositions No. 1, No. 2, No. 3, No. 4, No. 5 and No. 6, in accordance with the invention, are compatible with most mechanical pumps, as the photonic particles do not clog the orifices. The compositions may therefore be delivered in spray or light mist form, especially using the Yoshino Y70 or Panache SP22 pumps from the company Albea.

The invention claimed is:

1. A composition, comprising at least:
   photonic particles having an average size comprised from 0.5 μm to 100 μm and each including a diffracting arrangement of monodisperse nanoparticles or voids, the nanoparticles being constituted of silica, the diffraction spectrum of this arrangement including a reflection peak of the first order in the range of wavelengths ranging from 250 nm to 1800 nm,
   phenylbenzimidazole sulfonic acid,
   terephthalylidene dicamphor sulfonic acid, and
   at least one surfactant,
   wherein a mass ratio of photonic particles to surfactant is from 0.5 to 100.

2. The composition according to claim 1, in which the mass content of photonic particles is from 0.1% to 50% by weight relative to the total weight of the composition.

3. The composition according to claim 1, in which the photonic particles include aggregated nanoparticles.

4. The composition according to claim 1, in which the mean nanoparticle size is from 100 nm to 500 nm.

5. The composition according to claim 1, in which the photonic particles are substantially spherical in shape.

6. The composition according to claim 1, in which the photonic particles have a mean size from 1 μm to 40 μm.

7. The composition according to claim 1, in which the terephthalylidene dicamphor sulfonic acid mass content is from 0.01% to 60% by weight relative to the total weight of the composition.

8. The composition according to claim 1, in which the surfactant mass content is from 0.1% to 10% by weight relative to the total weight of the composition.

9. The composition according to claim 1, in which the surfactant is a surfactant with HLB greater than 7.

10. The composition according to claim 1, in which the surfactant is a water-soluble silicone including at least one monovalent terminal or pendant polyoxyalkylenated group.

11. The composition according to claim 1, further comprising water.

12. The composition according to claim 1, wherein the composition is anhydrous.

13. The composition according to claim 1, further comprising at least one polar solvent.

14. A photoprotective cosmetic composition comprising, in a physiologically acceptable medium, a composition according to claim 1.

15. The photoprotective cosmetic composition according to claim 14, having an SPF greater than or equal to 5.

16. A non-therapeutic photoprotection method for keratin substances against solar UV radiation, comprising applying a cosmetic composition according to claim 14 to said keratin substances.

17. A non-therapeutic cosmetic process for limiting the darkening of the skin and/or improving the colour and/or uniformity of the complexion, comprising a step of applying a cosmetic composition according to claim 14 to the skin.

18. The composition according to claim 1, further comprising at least one additional absorber, in addition to terephthalylidene dicamphor sulfonic acid and phenylbenzimidazole sulfonic acid, wherein said additional absorber is a molecule having an absorption spectrum in the UV-near IR domain (100 nm-3000 nm) whose mass extinction coefficient $\varepsilon_{1\%}$ is greater than or equal to 160 g$^{-1}$·100 mL·cm$^{-1}$, the absorber being at least an organic, water-soluble UV filter.

19. The composition according to claim 1, in which the mass ratio of photonic particles to surfactant is from 1 to 20.

\* \* \* \* \*